(12) United States Patent
Kojima et al.

(10) Patent No.: US 6,575,936 B1
(45) Date of Patent: Jun. 10, 2003

(54) LIQUID INFUSION APPARATUS

(75) Inventors: Seiji Kojima, Gunma (JP); Katumi Tominaga, Saitama (JP); Shigeo Hayashi, Hiroshima (JP); Hiromu Miura, Hiroshima (JP)

(73) Assignees: Japan Servo Co., Ltd., Tokyo (JP); JMS Co., Ltd., Hiroshima (JP)

( * ) Notice: Subject to any disclaimer, the term of this patent is extended or adjusted under 35 U.S.C. 154(b) by 140 days.

(21) Appl. No.: 09/672,292

(22) Filed: Sep. 27, 2000

Related U.S. Application Data

(62) Division of application No. 09/142,292, filed as application No. PCT/JP98/00064 on Jan. 9, 1998, now Pat. No. 6,179,569.

(30) Foreign Application Priority Data

| Jan. 10, 1997 | (JP) | 9-13199 |
| Jan. 10, 1997 | (JP) | 9-13205 |
| Jan. 10, 1997 | (JP) | 9-14448 |
| Jan. 10, 1997 | (JP) | 9-14763 |
| Jan. 10, 1997 | (JP) | 9-14764 |
| Jan. 10, 1997 | (JP) | 9-14768 |

(51) Int. Cl.⁷ .......................................... A61M 37/00
(52) U.S. Cl. ........................... 604/155; 604/131
(58) Field of Search ................. 604/65–67, 151, 604/152, 154, 155, 246, 207, 118, 121, 123, 131

(56) References Cited

U.S. PATENT DOCUMENTS

| 3,858,581 A | * | 1/1975 | Kamen ................... 128/218 A |
| 4,424,720 A | * | 1/1984 | Bucchianeri ............... 74/89.15 |
| 4,767,406 A | * | 8/1988 | Wadham et al. ............ 604/155 |
| 4,919,596 A | | 4/1990 | Slate et al. .................... 417/18 |
| 5,244,461 A | * | 9/1993 | Derlien ......................... 604/65 |
| 5,545,140 A | * | 8/1996 | Conero et al. .............. 604/154 |
| 5,814,015 A | * | 9/1998 | Gargano et al. ............. 604/67 |
| 5,879,360 A | * | 3/1999 | Crankshaw ................ 606/154 |

FOREIGN PATENT DOCUMENTS

| JP | 58-54709 | 4/1983 |
| JP | 63-44390 | 9/1988 |
| JP | 64-6833 | 2/1989 |
| JP | 1-297076 | 11/1989 |
| JP | 3-26771 | 4/1991 |
| JP | 4-2069 | 1/1992 |
| JP | 4-503916 | 9/1992 |
| JP | 9-122237 | 9/1992 |
| JP | 5-42218 | 2/1993 |
| JP | 8-4624 | 1/1996 |

* cited by examiner

*Primary Examiner*—Glenn K. Dawson
*Assistant Examiner*—Jennifer Maynard
(74) *Attorney, Agent, or Firm*—Patterson, Thuente, Skaar & Christensen, LLC

(57) ABSTRACT

A liquid infusion apparatus for fixing an outer cylinder of a syringe and a driver for pushing a plunger in a predetermined direction so as to exhaust liquid in the syringe, an incremental linear encoder arranged along the feeding axis of said driver for pushing the plunger, a detector of said incremental linear encoder mounted on a slider portion of the driver for pushing the plunger so as to generate a signal indicating a moving quantity of the plunger, and a sensor provided in the vicinity of a liquid exhaust port of the outer cylinder for setting along the feeding axis a remaining liquid quantity small section so as to generate a signal about a position of the plunger at the remaining liquid quantity small section.

19 Claims, 24 Drawing Sheets

CLOSED STATE

PERFECTLY OPENED STATE

SET STATE

PERFECTLY OPENED STATE

CLOSED STATE

SET STATE

CLOSED STATE

PERFECTLY OPENED STATE

PERFECTLY OPENED STATE

CLOSED STATE

PERFECTLY OPENED STATE

CLOSED STATE

LIQUID INFUSION APPARATUS

CROSS-REFERENCE TO RELATED APPLICATION

This application is a divisional application of Ser. No. 09/142,292 filed on Sep. 3, 1998 and allowed on Aug. 10, 2000, now U.S. Pat. No. 6,179,569, which is the National Stage of PCT/JP98/00064, filed Jan. 9, 1998.

TECHNICAL FIELD

The present invention relates to a liquid infusion apparatus, and more particularly, relates to a liquid infusion apparatus having a driving means for infusing liquid by pushing a plunger into a syringe.

BACKGROUND ART

FIG. 1 shows a conventional liquid infusion apparatus having a driving means comprising a CPU 1, a motor driving circuit 2, a potentiometer output processing circuit 3, an encoder output processing circuit 4, a motor 5, gears 6, a feed screw 7, a carriage 8, a slider 9 (plunger pushing out portion), a rotary encoder 10, a potentiometer 13, a hook 11 for operating the potentiometer 13, a wire 12, a syringe 14, and a plunger 15. In said conventional infusion apparatus shown in FIG. 1, the syringe 14 having the plunger 15 therein is mounted stationarily. The feed screw 7 is arranged in parallel with said syringe 14, connected to the motor 5 through the gears 6, and brought into engagement with the carriage 8. The slider 9 is connected to the carriage 8 and brought into engagement with an end of the plunger 15. The rotary encoder 10 is connected to the motor 5 or the feed screw 7. The potentiometer 13 is arranged at a position in parallel with the feed screw 7. The hook 11 is connected to an end of the wire 12 for rotating said potentiometer 13 and arranged so as to engage with the carriage 8 when the carriage 8 is moved to a remaining liquid quantity small section. The output of the rotary encoder 10 is applied to the CPU 1 through the encoder output processing circuit 4 and processed. The output of the potentiometer 13 is applied to the CPU 1 through the potentiometer output processing circuit 3 and processed. The motor is driven by a signal from the CPU 1 through the motor driving circuit 2, so that the plunger 15 is pushed out at a predetermined speed through a predetermined length to exhaust the liquid in syringe 14.

A further or second conventional liquid infusion apparatus shown in the Japanese Patent Application Laid-Open No. 42218/93 comprises a driving means for driving a plunger of a syringe to move at a predetermined speed between a first and a second positions, and a first linear encoder arranged between a third and fourth positions corresponding to the first and second positions, respectively, for detecting the absolute position and the moving distance of said plunger. FIG. 2 shows the essential portion thereof.

In the first conventional apparatus, no actual feeding quantity of the carriage can be detected in case that a slip is generated about the feed screw or the motor, or the carriage is floated on the feed screw, and no actual position of the remaining liquid quantity small section can be detected in case that the wire is cut, or the contact of the electric terminal of the potentiometer is failure. Further, in the second conventional apparatus, such problems that the actual feeding quantity of the carriage can not be detected because of the slip about the feed screw or the motor, or of the floatation of the carriage on the feed screw can be solved, because in the second conventional apparatus, the moving state of the carriage is detected by the linear encoder. However, the second conventional apparatus has such a problem that the linear encoder for detecting the absolute value is expensive and the skill is required. Accordingly, an object of the present invention is to provide a liquid infusion apparatus having a driving means which can detect exactly and control the movement of the plunger so as to solve the above problems.

Further, Japanese Patent Application Laid-Open No. 44390/88 discloses an improved liquid infusion apparatus comprising a feed screw to be driven by a prime mover, and a slider movable linearly, wherein the slider is brought into engagement with said feed screw so as to push out a plunger in a syringe and to exhaust liquid in the syringe, and a pressure exerted on the plunger by the slider is detected and compared with a reference value to generate a warning signal.

In said liquid infusion apparatus, a pressure sensor is provided at a plunger pushing portion of the slider and an output of the sensor is compared with a plurality of reference values so as to generate the warning signal and to carry out safely the infusion. As shown in FIG. 3, however, in said liquid infusion apparatus an end of the plunger is brought into contact simply with the slider, and accordingly in case that the plunger is sucked into the syringe by an attractive force due to the negative pressure applied to the syringe, the slider is brought into disengagement with the plunger, so that the liquid infusion cannot be attained, but such state cannot be detected. Accordingly, the other object of the present invention is to provide a liquid infusion apparatus which can detect the negative pressure applied to the plunger.

FIGS. 4A and 4B are views explaining the operation of the other conventional liquid infusion apparatus. FIG. 4A shows such a state that the syringe 14 and the plunger 15 are not yet mounted on the main body of the apparatus. FIG. 4B shows such a state that the syringe 14 and the plunger 15 are mounted on the main body. In FIGS. 4A and 4B, a reference numeral 14-1 denotes a flange of the syringe 14, a reference numeral 15-1 denotes a flange of the plunger 15. A reference numeral 16 denotes a slider, 16-1 denotes a holding member provided at the slider 16 for holding the flange 15-1 of the plunger 15, 16-2 denotes a pushing portion of the slider 16, 16-3 denotes a grooved portion formed on the holding member 16-1, and 17 denotes a lever of a slider unlock means (not shown). A reference numeral 17-1 denotes a push button of the lever 17, 17-2 denotes a pivot shaft of the lever 17, 21 denotes a main body of the liquid infusion apparatus, and 21-1 denotes a groove provided at the main body 21 for receiving therein the flange 14-1 of the syringe 14. In order to install the syringe 14 and the plunger 15 to the main body 21 of the liquid infusion apparatus shown in FIG. 4A, the slider 16 is disengaged from the feed screw 7 by pushing the pushing button 17-1 of the lever 17, the slider 16 is moved toward the flange 15-1 of the plunger 15, and the pushing portion 16-2 is brought into contact with an outer end of the plunger 15, so that the syringe 14 and the plunger 15 are fixed to the main body 21 as shown in FIG. 4B. The width of the grooved portion 16-3 is determined corresponding to the maximum thickness of the flange 15-1 of the plunger 15.

In the above conventional apparatus, however, the width of the grooved portion 16-3 of the holding member 16-1 is fixed, and accordingly, if the thickness of the flange 15-1 of the plunger 15 is smaller than that of the grooved portion, the plunger 15 cannot be held positively by the slider 16.

Further, in a liquid infusion apparatus wherein the liquid infusion is carried out automatically by moving the plunger of the syringe using a motor, it is necessary absolutely to prevent the plunger from moving in a (suction) direction contrary to the pushing direction of the plunger. Accordingly, in the conventional liquid infusion apparatus, the rotary direction of the motor is limited to only one direction by a motor driving program and an electric circuit thereof.

Recently, however, most of electric appliances generate many kinds of electric noises (electromagnetic waves) according to the development of the electronic systems, so that many problems of wrong operation due to the noises have been encountered in the field of the medical services.

Further, Japanese Utility Model Application Laid-Open No. 89053/83 discloses an improved liquid infusion apparatus comprising a feed screw driven by a prime mover, and a slider movable linearly, engaged with the feed screw so as to push out the plunger of the syringe and infuse liquid from the syringe, wherein the engagement and disengagement of the slider with the feed screw can be carried out corresponding to that of the slider with the syringe. In said conventional infusion apparatus, as shown in FIGS. 5A and 5B, a sliding means is provided at a driving pawl which is fitted into a driving member when the syringe is installed on the main body, so that a feed screw is disengaged from a half-nut fixed to said driving member at the same time of the sliding of the driving pawl. Japanese Patent Application Laid-Open No. 247347/91 discloses a further conventional liquid infusion apparatus as shown in FIG. 6. In this apparatus, a movable block is provided movably reciprocally in an axial direction of a syringe and connected to a driving means, and a pushing portion of a plunger is provided at the movable block movably reciprocally between a position where the pushing portion is engaged with the plunger and a position where the pushing portion is disengaged from the plunger, and a half-nut is engaged with and disengaged from a feed screw according to the movement of the movable block.

The apparatus shown in FIGS. 5A and 5B, or shown in FIG. 6 has such problems that in the loading state the half-nut is floated on the feed screw, because the half-nut is normally urged to the feed screw by a spring, so that the precise feeding operation cannot be carried out. Further, in the conventional apparatus, operations for engaging the plunger with the slider and for disengaging the plunger from the slider are carried out at the same time with operations for engaging the feed screw with the half-nut and for disengaging the feed screw from the half-nut. However, only a simple groove is provided at a holding portion of the slider for holding a flange of the plunger, so that the flange of the plunger is held unsteadily by the holding member due to the difference between the thickness of the flange of the plunger and the width of groove formed on the holding portion of the slider, which are generated by the mechanical precision. In the conventional apparatus mentioned above, it is preferable generally to shape the feed screw so as to have teeth of rectangular in cross section, which is in parallel with a vertical plane normal to the feeding direction of the feed screw, in order to prevent the half-nut from floating from the feed screw in case of loading. However, there are two problems. One problem is that the feed screw having teeth of the rectangular cross section is high in manufacturing cost, because the manufacturing steps thereof are limited. The other problem is that the flange of the plunger cannot be held precisely by the holding member, because a gap is formed between the flange of the plunger and the groove of the holding member due to the manufacturing precision.

The task of the present invention is to solve the above problems and to provide a liquid infusion apparatus of high precision and inexpensive.

DISCLOSURE OF THE INVENTION

A liquid infusion apparatus according to the present invention has means for fixing an outer cylinder of a syringe and driving means for pushing a plunger in a predetermined direction so as to exhaust liquid in the syringe, and is characterized by comprising an incremental linear encoder arranged along the feeding axis of said driving means for pushing the plunger, detecting means of said incremental linear encoder mounted on a slider portion of said driving means for pushing the plunger, means for processing an output of said detecting means, applying to an UP/DOWN counter and comparing with an initial value inputted previously so as to generate a signal indicating a moving quantity of said plunger, and a sensor provided in the vicinity of an end of said outer cylinder for setting along said feeding axis a remaining liquid quantity small section, wherein said counter is reset or the counted value is memorized and then the counting is started by an output of said sensor so as to determine a position of the plunger at said remaining liquid quantity small section. According to the above construction, the moving quantity and the position of the carriage for moving the plunger can be detected directly by an inexpensive incremental linear encoder. Further, the absolute position at the remaining infusion liquid quantity small section can be recognized in non-contact manner by counting feedback pulses from the encoder after that the carriage is passed across the detecting sensor for detecting the starting point of the remaining infusion liquid quantity small section.

In a liquid infusion apparatus according to the present invention, a holding arm for holding a flange of a plunger is provided rotatably and movably in a movable direction of a slider so as to push the flange of the plunger to the slider by the holding arm for holding.

According to the liquid infusion apparatus as mention above, the flange of the plunger can be held precisely by the slider, even if the size of the syringe is varied, because the flange of the plunger is pushed to the slider by the holding arm for holding.

Further, a liquid infusion apparatus of the present invention has a holding arm for pushing the flange of said plunger in a direction reverse to a pushing direction of the plunger toward a plunger holding portion of said slider for holding, a pressure sensor provided at said plunger holding portion of the slider, and a processing circuit for comparing an output of said pressure sensor with a plurality of reference values to generate a processing signal.

In said liquid infusion apparatus, even if a force stronger than a pressure acting on the plunger by the slider is applied to the plunger so that the plunger is to be sucked into the syringe (negative pressure state), the plunger can be held by the slider, and a negative pressure state can be detected by comparing an output of said pressure sensor in case that the flange of said plunger is held by the plunger holding portion by the holding arm with the reference values.

Further, a liquid infusion apparatus according to the present invention has a feed screw driven by a prime mover and a slider movable linearly and engaged with said feed screw so as to push a plunger of a syringe for exhausting liquid in the syringe, and is characterized by comprising a lever supported rotatably freely by a first shaft arranged horizontally and normally to a moving direction of said slider, a push button provided at one end of said lever so as to project from said slider, a slider releasing device, an interlocking rod interlocking with said slider releasing device, the other end of said lever being contacted with said interlocking rod, holding means supported by said slider rotatably by a second shaft, which is in parallel to said first shaft for press holding the flange of the plunger by the slider, a spring for urging the holding means to rotate in the clockwise direction, and interlocking means for interlocking said holding means with said lever.

In the above construction, the flange of the plunger can be held positively by the slider, even if the size of the thickness of the flange of the plunger is varied, because the flange of the plunger is pushed to the slider by the holding arm for holding.

Further, a liquid infusion apparatus of the present invention is characterized by comprising a half-nut releasing device interlocking with a releasing lever mounted on the slider, said half-nut releasing device comprising means for engaging the feed screw with the half-nut and disengaging the feed screw from the half-nut moved by a releasing cam having a step portion, and means for pushing the flange of the plunger to the slider by the holding arm for holding. Further, the cross section of the tooth of the feed screw is inclined to a plane normal to the feeding direction of the screw, so that the feed screw can be manufactured by the form rolling process etc. in mass production basis.

In the above construction, the releasing cam of the half-nut releasing device is moved in the forward direction of the interlocking rod to urge the half-nut to the feed screw, so that the releasing cam receives a component force in the vertical direction of a force applied to the half-nut on loading, thereby causing the half-nut is prevented from floating.

Further, the flange of the plunger is pushed to the slider by the arm provided at the slider, the flange is held positively by the slider and no gap is formed between the contact portion of the slider and the end of the plunger, so that the movements of the slider and the plunger coincide perfectly with each other and precise liquid infusion can be realized.

Further, a liquid infusion apparatus according to the present invention has a feed screw driven by a prime mover and a slider movable linearly and engaged with said feed screw so as to push a plunger of a syringe for exhausting liquid in the syringe, and is characterized in that means for transmitting a driving force only in a syringe pushing direction is inserted between the feed screw and the prime mover.

In the liquid infusion apparatus according to the present invention, a mechanical backstop is provided between a rotary shaft of the electric motor and the feed screw, so that even if the electric motor is rotated reversely by the external noise the feed screw is prevented from rotating reversely, and the danger of the malfunction can be avoided.

The other objects and features of the present invention will become apparent from the following descriptions in conjunction with the accompanying drawings.

BEST MODE FOR CARRYING OUT THE INVENTION

Figure 1:
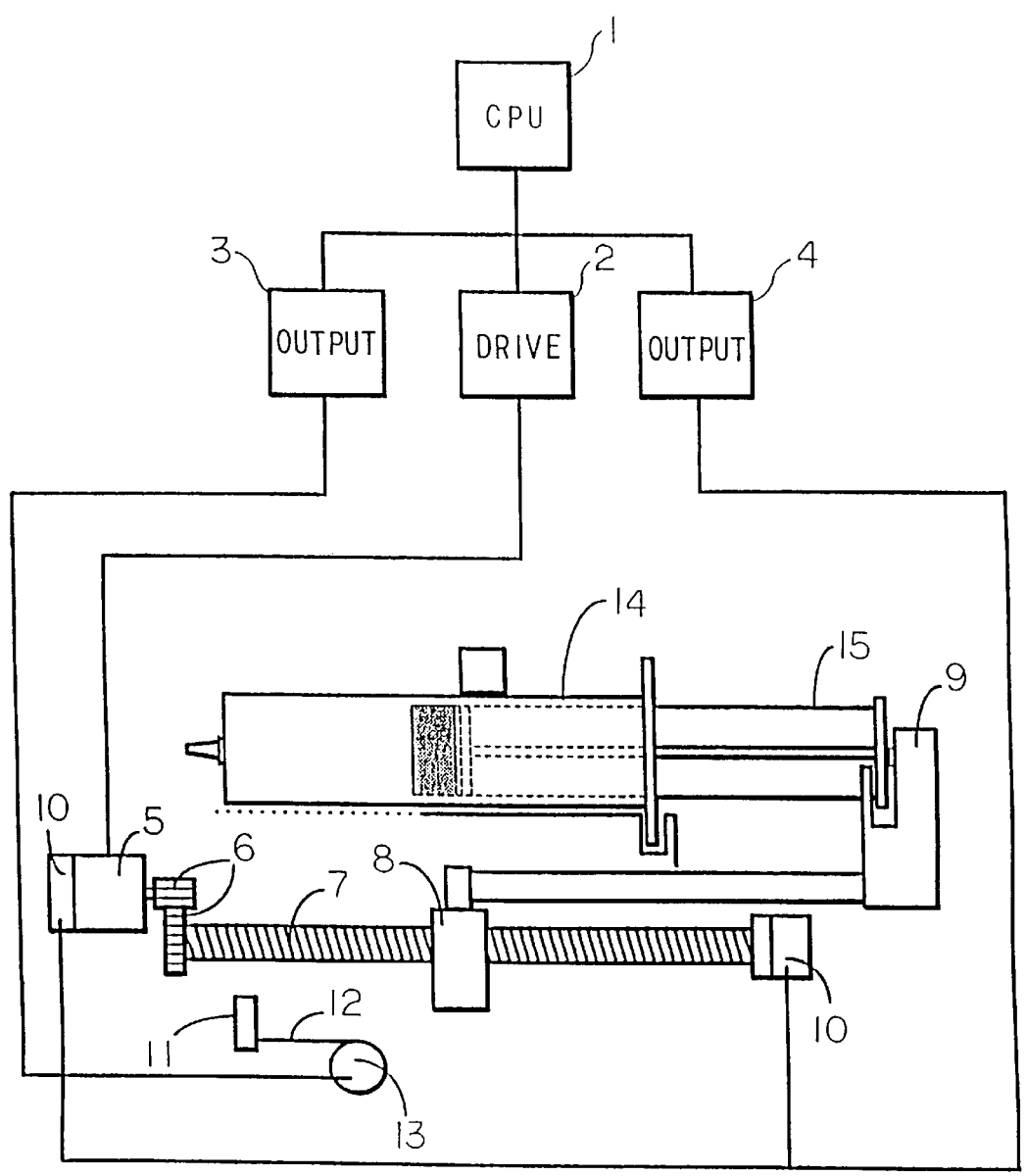
FIG. 1 illustrates a schematic view of the construction of a conventional liquid infusion apparatus.
Figure 7:
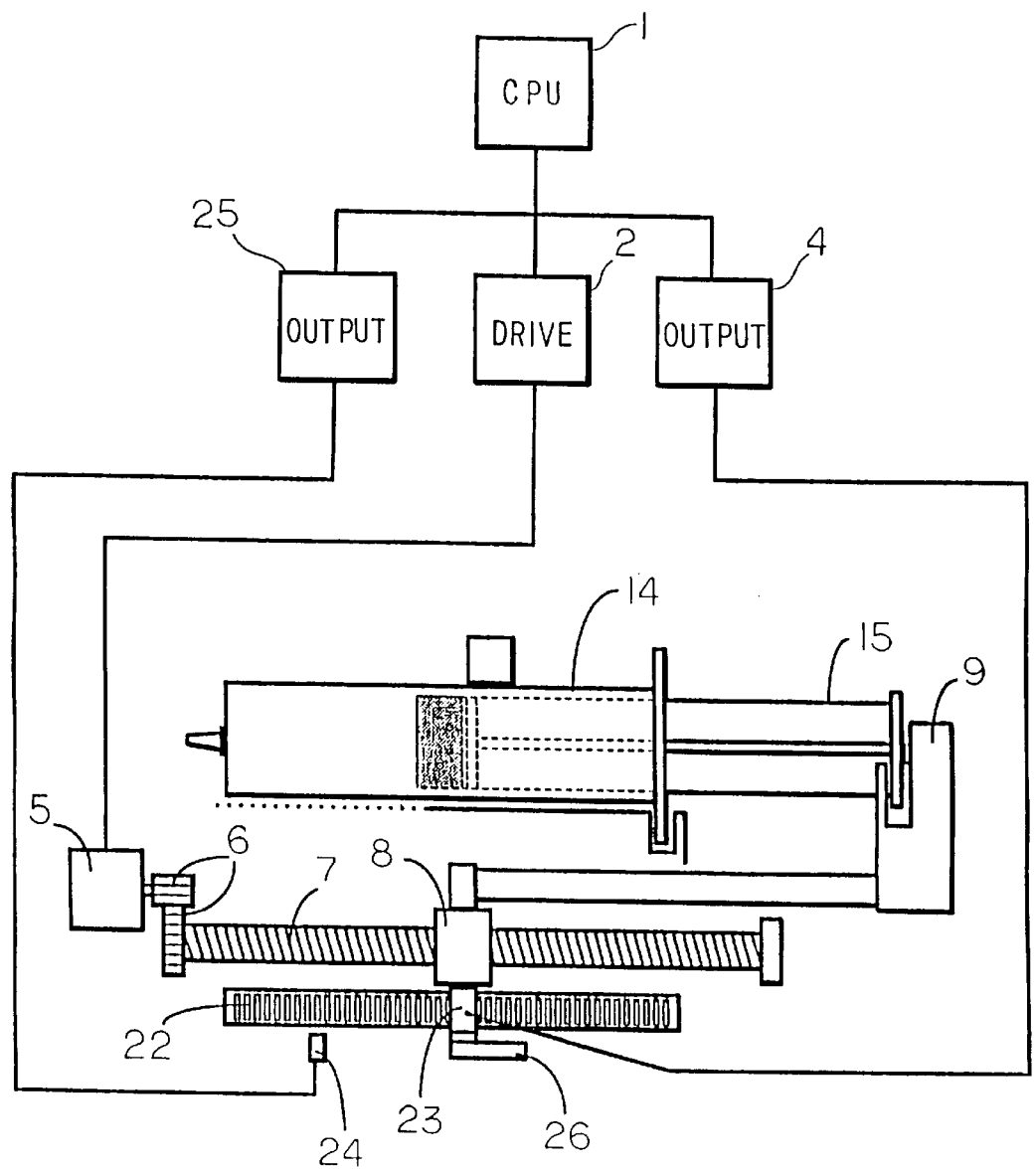
FIG. 7 illustrates a schematic view of a liquid infusion apparatus according to the present invention.

The present invention will now be explained with reference to the drawings. FIG. 7 is a schematic view of a liquid infusion apparatus according to the present invention. Parts of the apparatus which are similar to corresponding parts of the conventional apparatus shown in FIG. 1 have been given corresponding reference numerals and need not be further redescribed. As shown in FIG. 7, a plate 22 of a linear encoder is provided in parallel with a feeding screw 7, and a photo-coupler 23 of a carriage 8 is provided so as to face to said plate 22. A sensor 24 is provided in the vicinity of an end of said plate 22 corresponding to an end of a syringe 14. A dog 26 is provided on said carriage 8 so as to actuate said sensor 24. An output of said photo-coupler 23 is applied to a CPU 1 through an encoder output processing circuit 4, and an output of said sensor 24 is applied to the CPU 1 through a sensor output processing circuit 25.

As shown in FIG. 7, an incremental linear encoder is composed of the plate 22 arranged in parallel with the feeding screw 7, and the photo-coupler 23 fixed to the carriage 8, which is stationarily engaged with a slider 9. Further, the dog 26 for a remaining liquid quantity small section is mounted on the carriage 8, and the sensor 24 for the remaining liquid quantity small section is actuated by the movement of the carriage 8.

In operation, a pulse signal generated between the plate 22 with slits and the photo-coupler 23 mounted on the carriage 8 is processed in the encoder output processing circuit 4 and applied to the CPU 1 as an information to show the movement of the carriage 8, so that the movement of the carriage 8 can be monitored directly.

Furthermore, a signal generated when the dog 26 mounted on the carriage 8 is moved across the sensor 24 is processed by the sensor output processing circuit 25 and applied to the CPU 1 as an information of position. Then an encoder feedback pulse obtained by processing the pulse signal generated from the photo-coupler 23 by the encoder output processing circuit 4 is applied to an UP/DOWN counter and compared with an initial value applied to the UP/DOWN counter previously to recognize in non-contact manner an absolute position of the plunger at the remaining liquid quantity small section.

Figure 8A:
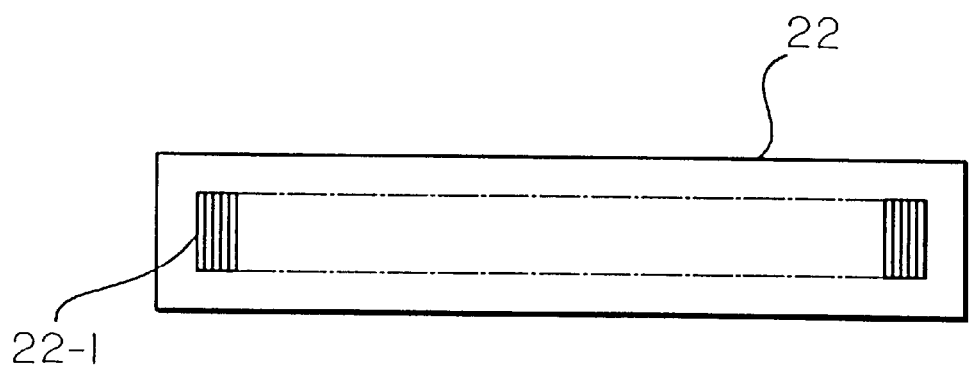
FIG. 8A illustrates a schematic view of a slit plate of an incremental encoder for use in a liquid infusion apparatus according to the present invention.
Figure 8B:
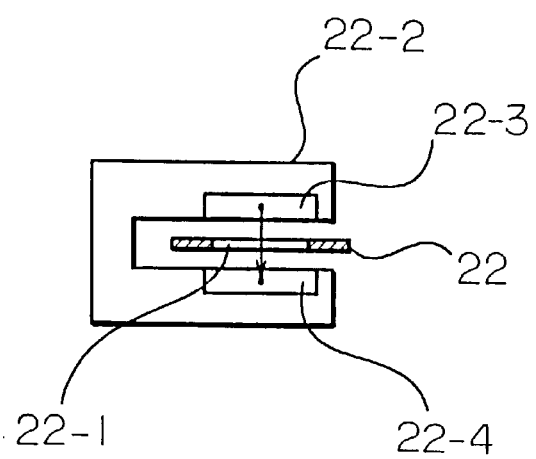
FIG. 8B illustrates a view of the incremental encoder according to the present invention using the slit plate shown in FIG. 8A.
Figure 8C:
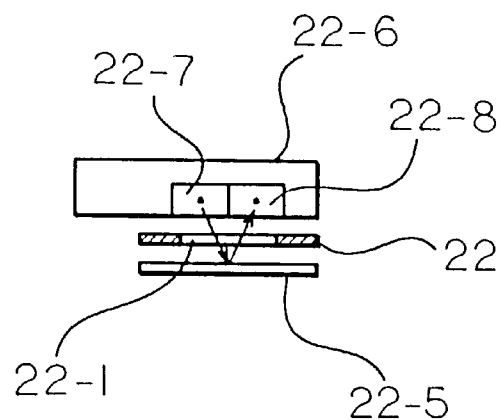
FIG. 8C illustrates a view of the incremental encoder according to the present invention using a reflecting plate.

As shown in FIGS. 8A and 8B, an example of an optical incremental linear encoder for use in the liquid infusion apparatus according to the present invention comprises an opaque planar plate 22 having fine slits 22-1 equidistantly apart from one another, and a photo-coupler 22-2 consisting of a light emitting element 22-3 and a light receiving element 22-4, wherein a pulse signal is obtained when the slit 22-1 of the plate 22 is moved across the optical axis of said photo-coupler 22-2. As shown in FIG. 8C, an optical incremental linear encoder of the other embodiment of the present invention comprises the plate 22 with the slits, a light reflecting plate 22-5 arranged in the vicinity of and in parallel with said plate 22, and a photo-coupler 22-6 consisting of a light emitting element 22-7 and a light receiving element 22-8 arranged at the opposite side of the light reflecting plate 22-5 with respect to the plate 22, wherein a pulse signal can be obtained corresponding to a reflected light reflected from the light reflecting plate 22-5 through the slit 22-1 of the plate 22. Both optical incremental linear encoders are the same in function with each other and can be used similarly.

Figure 2:
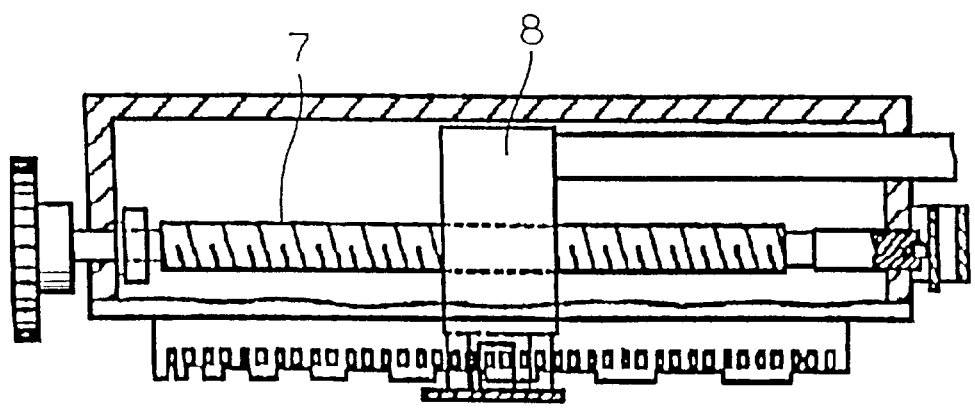
FIG. 2 illustrates a schematic view of the construction of a linear encoder of the conventional liquid infusion apparatus.
Figure 3:
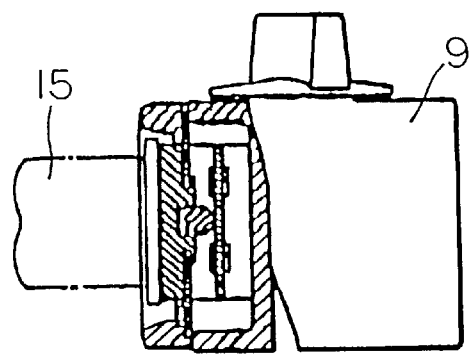
FIG. 3 illustrates a view of an essential portion of a pressure sensor on a slider mounting portion in the conventional liquid infusion apparatus.
Figure 4A:
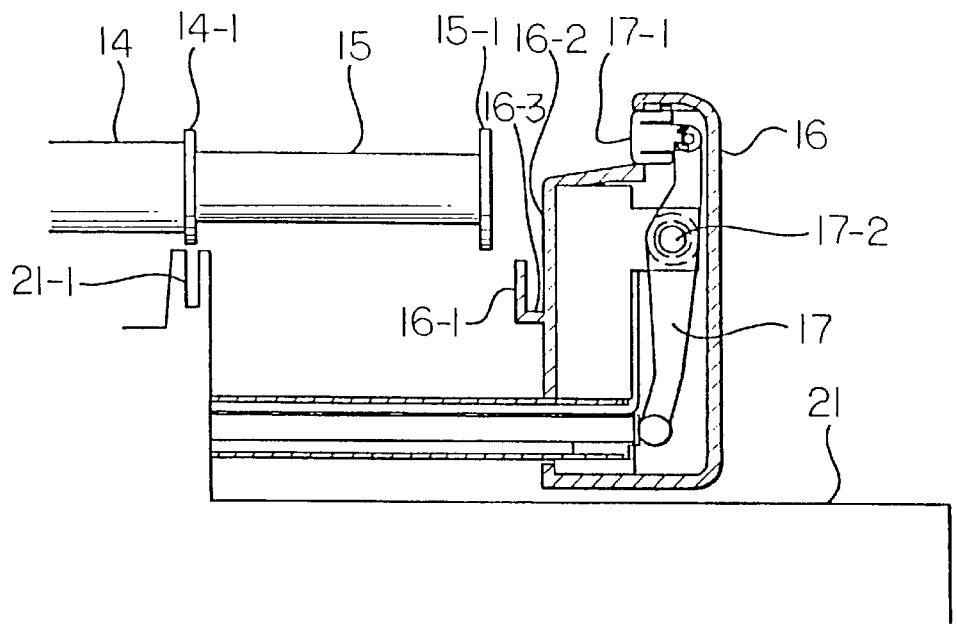
FIG. 4A illustrates a side view of an essential portion in a state that an end of a plunger is not yet held by the slider of the conventional liquid infusion apparatus.
Figure 4B:
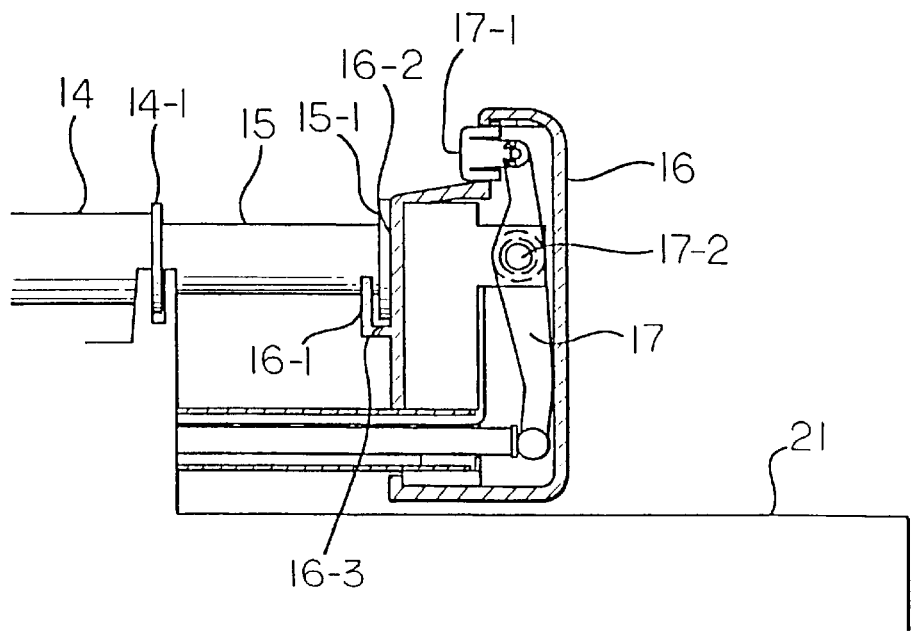
FIG. 4B illustrates a vertical sectional side view of an essential portion in a state that the end of the plunger is held by the slider of the conventional liquid infusion apparatus.
Figure 5A:
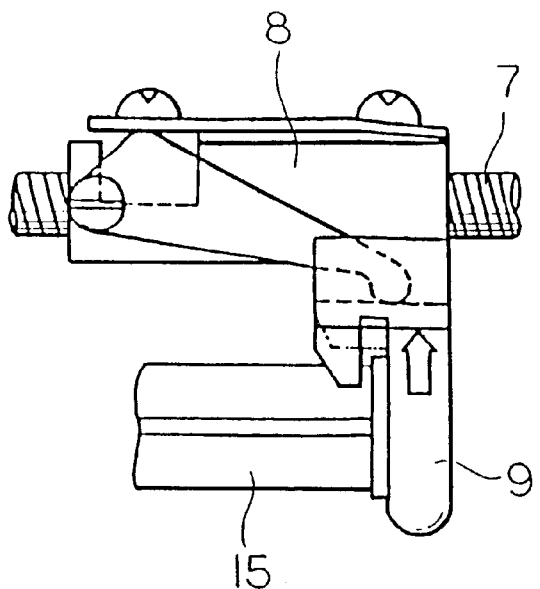
FIG. 5A illustrates a view of the conventional liquid infusion apparatus.
Figure 5B:
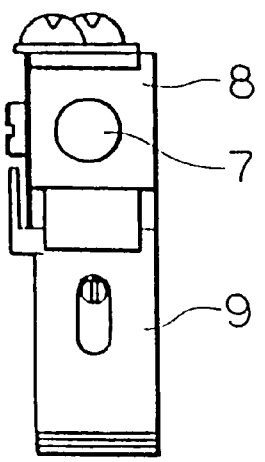
FIG. 5B illustrates a side view of the liquid infusion apparatus shown in FIG. 5A.
Figure 6:
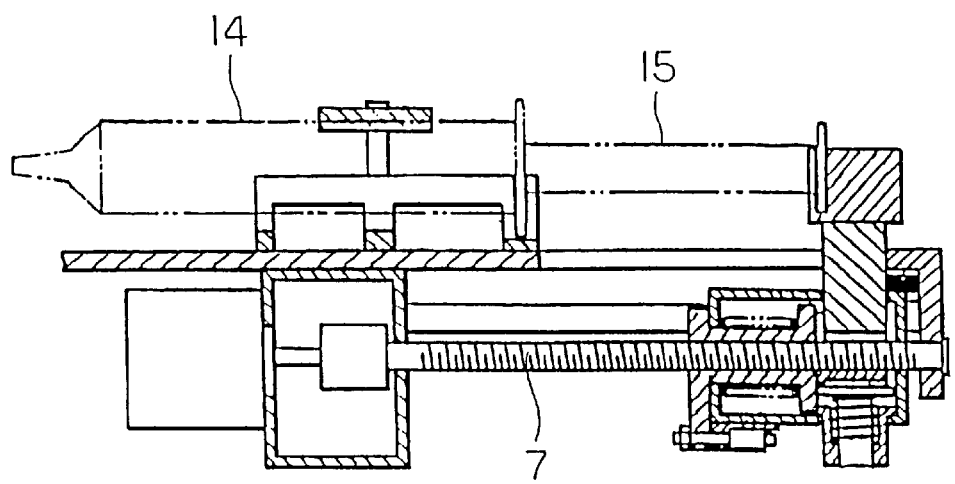
FIG. 6 illustrates a view of the conventional liquid infusion apparatus.

As stated above, the incremental linear encoder having the opaque planar plate having the fine slits equidistantly apart from one another for use in the liquid infusion apparatus of the present invention is simple in construction and low in manufacturing cost compared with the conventional absolute value type linear encoder shown in FIG. 2, wherein a plurality of transparent sections of which width is narrower in consecutive order are formed on both of the transparent and non-transparent portions. The incremental encoder of the present invention has such features that the plate with slits can be manufactured low in cost and that a high precision detecting signals of the moving speed, the moving distance and the absolute position etc. of the plunger can be obtained economically by processing and converting the output by a processing circuit.

In place of the optical type incremental linear encoder shown in FIG. 8, a magnetic type incremental linear encoder wherein a magnetic scale plate having N poles and S poles formed alternately with a constant pitch is arranged at a position of the slit plate, and a magnetic detection device is arranged at a position of the photo sensor, can be used.

According to the liquid infusion apparatus having the above structure of the present invention, the detection's of the moving distance of the plunger and the absolute position of the plunger at the liquid remaining area can be realized in non-contact manner by detecting the actual motion of the carriage for pushing out the plunger.

Figure 9A:
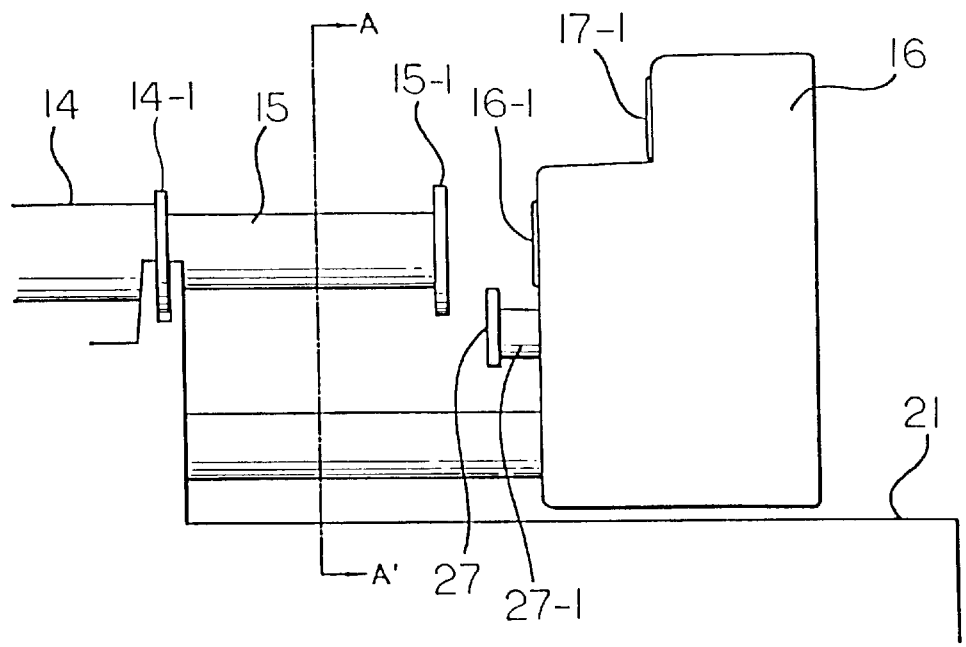
FIG. 9A illustrates a side view of an essential portion in a state that the end of the plunger is not yet held by the slider of a liquid infusion apparatus according to an embodiment of the present invention.
Figure 9B:
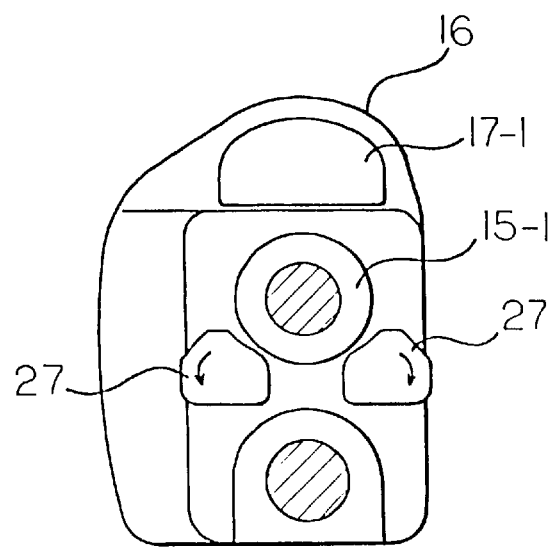
FIG. 9B illustrates a view, taken along lines A–A' of FIG. 9A.
Figure 10A:
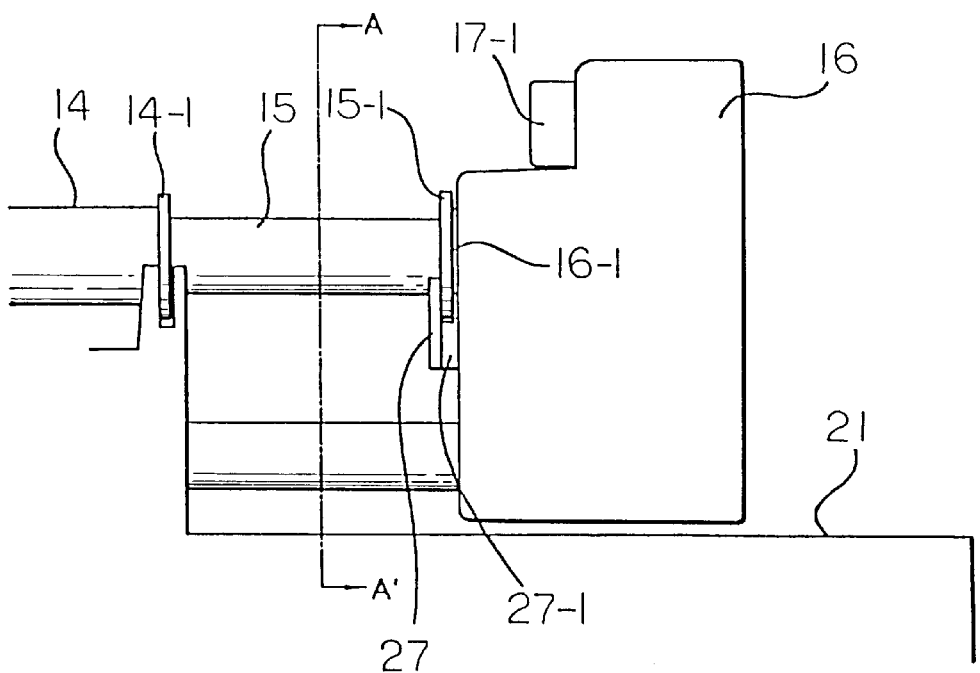
FIG. 10A illustrates a side view of an essential portion in a state that the end of the plunger is held by the slider of the liquid infusion apparatus according to an embodiment of the present invention.
Figure 10B:
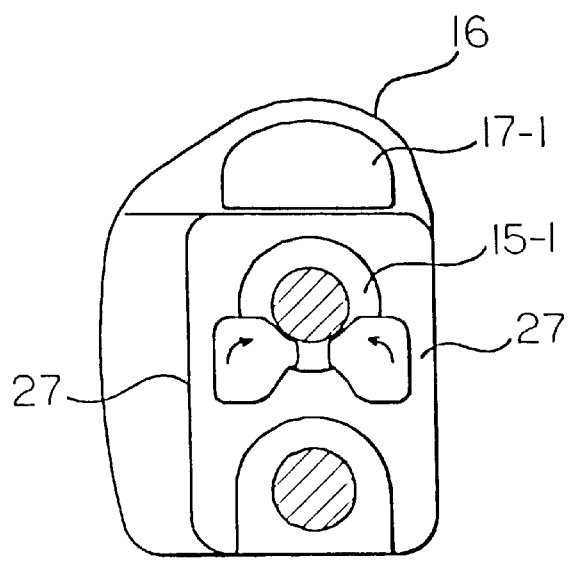
FIG. 10B illustrates a view, taken along lines A–A' of FIG. 10A.

Another embodiment of the present invention will now be explained with reference to FIGS. 9-11. FIGS. 9A and 9B show a state that the flange of the plunger in the syringe is not yet held by the slider portion. FIG. 9A is a side view of the essential portion of the apparatus according to the present invention, and FIG. 9B is a front view, taken along the lines A–A' of FIG. 9A and viewed in the direction of arrow. FIGS. 10A and 10B show a state that the flange of the plunger in the syringe is held by the slider portion. FIG. 10A is a side view of the essential portion of the apparatus according to the present invention, and FIG. 10B is a front view, taken along the lines A–A' of FIG. 10A and viewed in the direction of arrow.

In FIGS. 9A and 9B, if a push button 17-1 is pushed, the holding arms 27 of a slider 16 for holding the flange of the plunger are rotated around shafts 27-1, and opened so that the slider 16 can be approached to the end of said plunger without contacting with the holding arms 27. Then, as shown in FIG. 10A, the slider 16 is moved in the leftward direction in FIG. 9A so that a contact surface 16-1 of the slider 16 is brought into contact with the end surface of the plunger 15. When the push button 17-1 of the slider 16 is retracted, the holding arms 27 are rotated so as to engage with the flange 15-1 of the plunger as shown in FIG. 10B, and the slider 16 is approached to the flange of the plunger for holding.

Figure 11A:
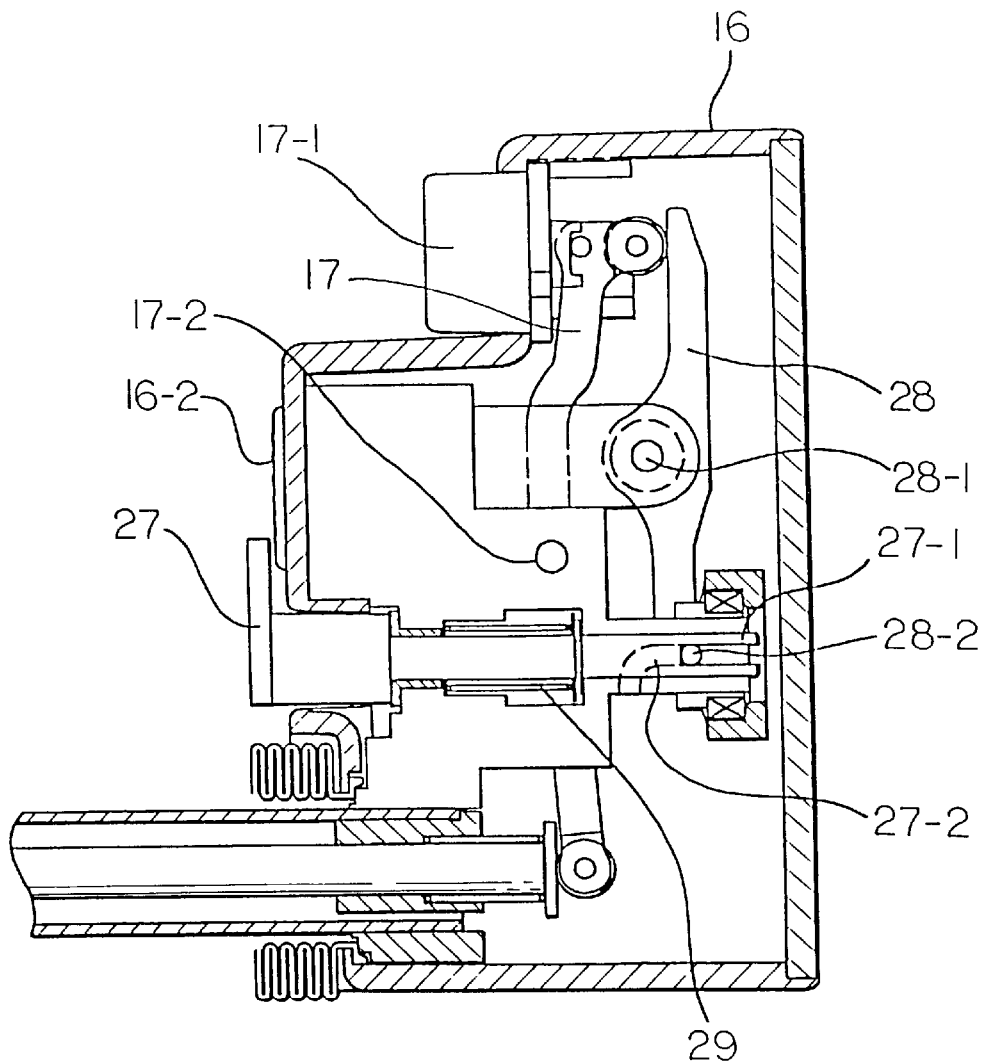
FIG. 11A illustrates a vertical sectional side view of an essential portion of the slider of a liquid infusion apparatus according to an embodiment of the present invention.
Figure 11B:
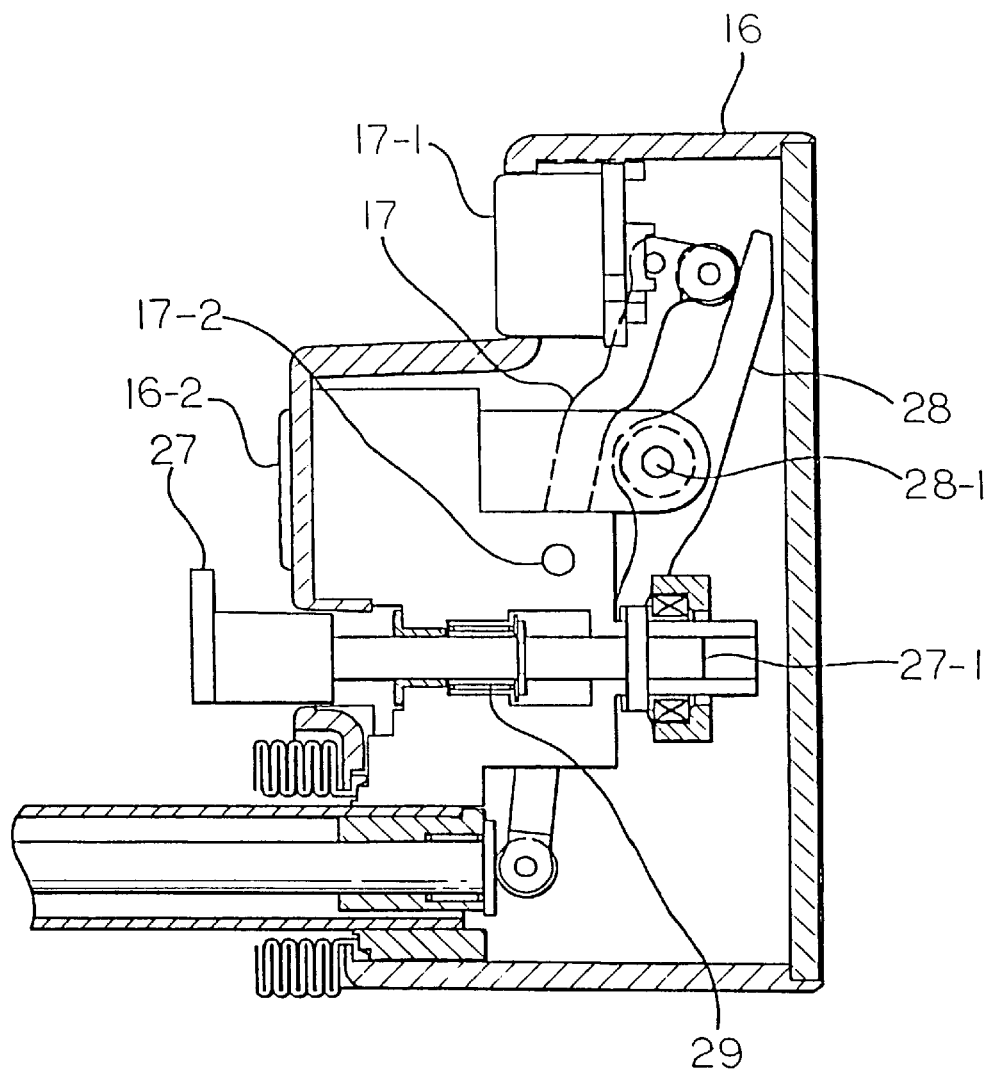
FIG. 11B illustrates a vertical sectional side view of an essential portion of the slider of a liquid infusion apparatus according to an embodiment of the present invention.
Figure 11C:
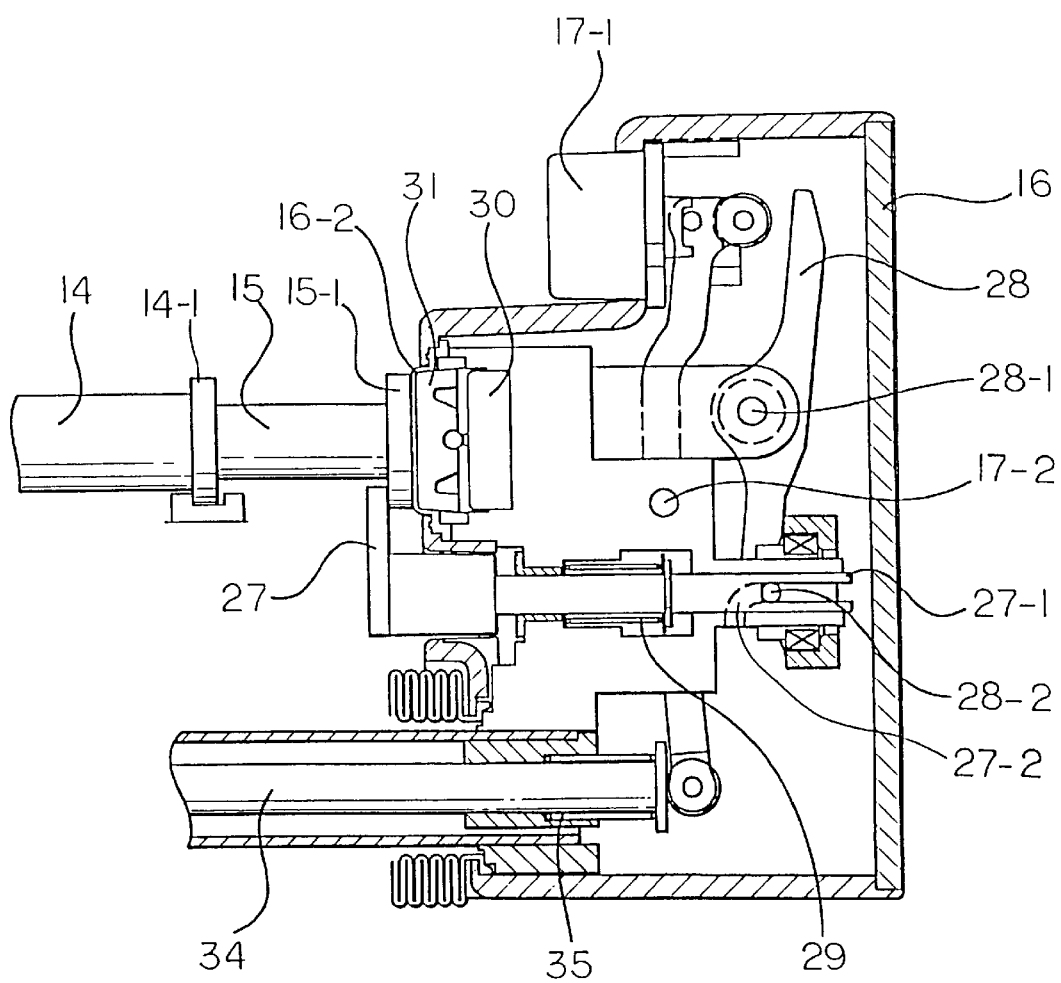
FIG. 11C illustrates a vertical sectional side view of an essential portion of the slider of a liquid infusion apparatus according to an embodiment of the present invention.

FIGS. 11A to 11C are views for explaining the essential portions of the slider 16 shown in FIGS. 9A and 9B, and FIGS. 10A and 10B. FIG. 11A shows a state that the holding arms 27 for holding the flange of the plunger are closed. FIG. 11B shows a state that the holding arms 27 are opened. FIG. 11C shows a state that the syringe 14 and the plunger 15 are held by the slider 16. In FIGS. 11A to 11C, a reference numeral 27-2 denotes a screw groove on the shaft 27-1, a reference numeral 28 denotes a driving lever of the holding arm 27, 28-1 denotes a shaft for the lever 28, 28-2 denotes an engaging pin engaging with the screw groove 27-2, and 29 denotes a return spring. Two holding arms 27 and parts corresponding thereto are provided so as to be rotated in the directions opposite to each other.

In FIG. 11B, if the push button 17-1 of the releasing device (not shown) for the slider is pushed, the driving lever 28 for the holding arms 27 is rotated centering around the shaft 28-1, so that the shafts 27-1 of the holding arms 27 are moved in the leftward direction against the return springs 29 because the engaging pin 28-2 is engaged with the screw groove 27-1 on the shaft 27-1 of the holding arm 27. At the same time, the shafts 27-1 are rotated in the counter-clockwise direction by the action of the engaging pins 28-2 and the screw grooves 27-2, so that the holding arms 27 for holding the flange of the plunger are opened. As shown in FIG. 11A, when the push button 17-1 is returned the lever 17 of the releasing device is returned and the driving lever 28 of the holding arms 27 is also returned. Accordingly, the shafts 27-1 are moved in the rightward direction by the action of the engaging pins 28-2 and the screw grooved 27-2, so that the holding arms 27 are closed. In FIG. 11A, the holding arms 27 approach to a contact portion 16-2 of the plunger, because the syringe 14 is not yet mounted. FIGS. 11A and 11B show a state that the push button 17-1 is operated in the absence of the syringe. As shown in FIG. 11C, if the push button 17-1 is returned in a state that the flange 15-1 of the plunger 15 is contacted with the contact portion 16-2 of the slider 16, the holding arms 27 urge the flange 15-1 of the plunger to the contact portion 16-2 of the slider 16 for holding. In the state shown in FIG. 11C, two holding arms 27 urge the flange 15-1 to the contact portion 16-2 of the slider with the force of the return spring 29 for holding, so that the flange 15-1 of the plunger can be held positively by the slider 16, ever if the thickness of the flange 15-1 is varied.

In case that the syringe 14 is to be released from the main body 21 of the liquid infusion apparatus, the syringe 14 can be released easily from the main body 21, because two holding arms 27 are opened when the push button 17-1 is pushed.

According to the liquid infusion apparatus of the present invention having the above construction, by pushing the push button when the syringe is installed in the main body of the liquid infusion apparatus, the holding arms for holding the flange of the plunger are moved in the moving direction of the slider and rotated to hold the flange of the plunger easily, and by returning the push button the holding arms urge the flange to the slider for holding. Accordingly, the flange can always be held by the slider positively even if the size of the syringe is changed.

Figure 12A:
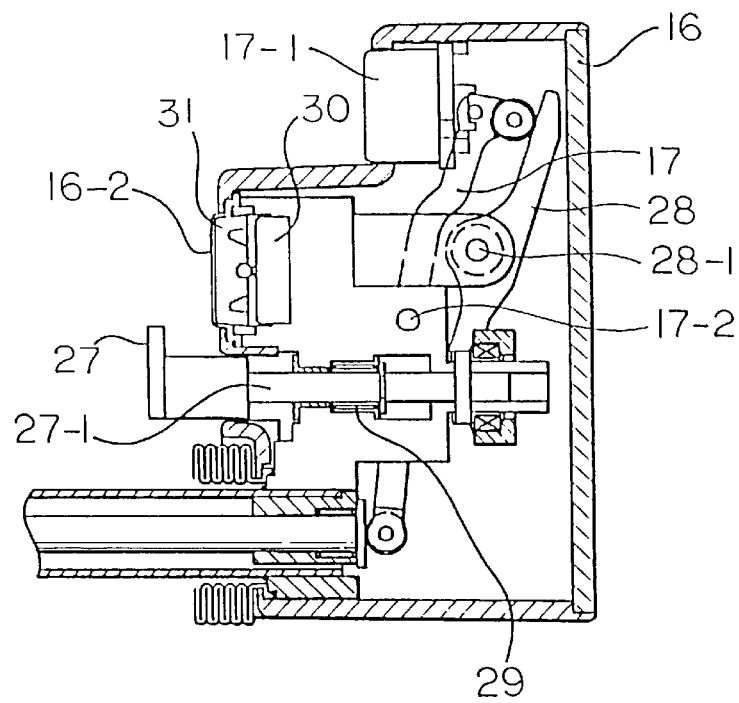
FIG. 12A illustrates a sectional view of an essential portion of the slider of a liquid infusion apparatus according to another embodiment of the present invention.
Figure 12B:
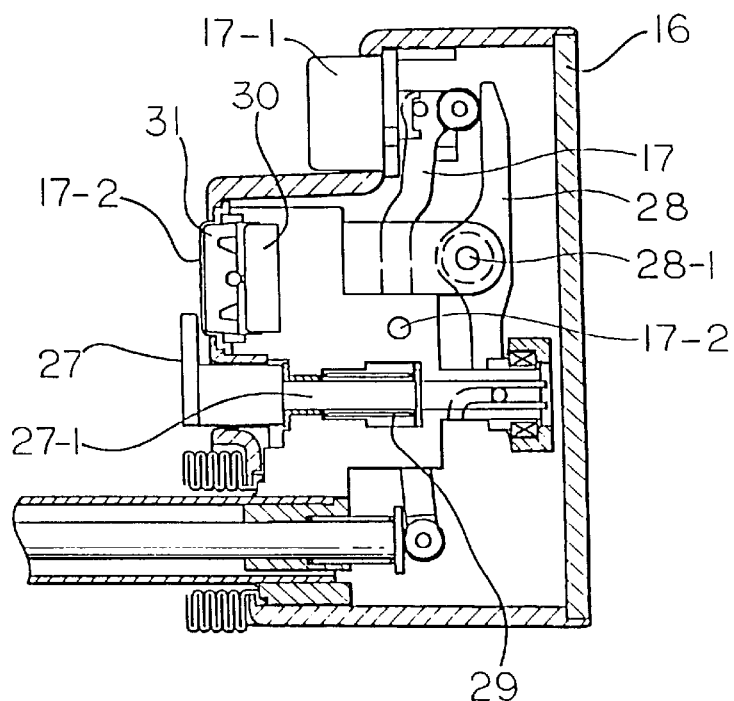
FIG. 12B illustrates a sectional view of an essential portion of the slider of a liquid infusion apparatus according to another embodiment of the present invention.
Figure 12C:
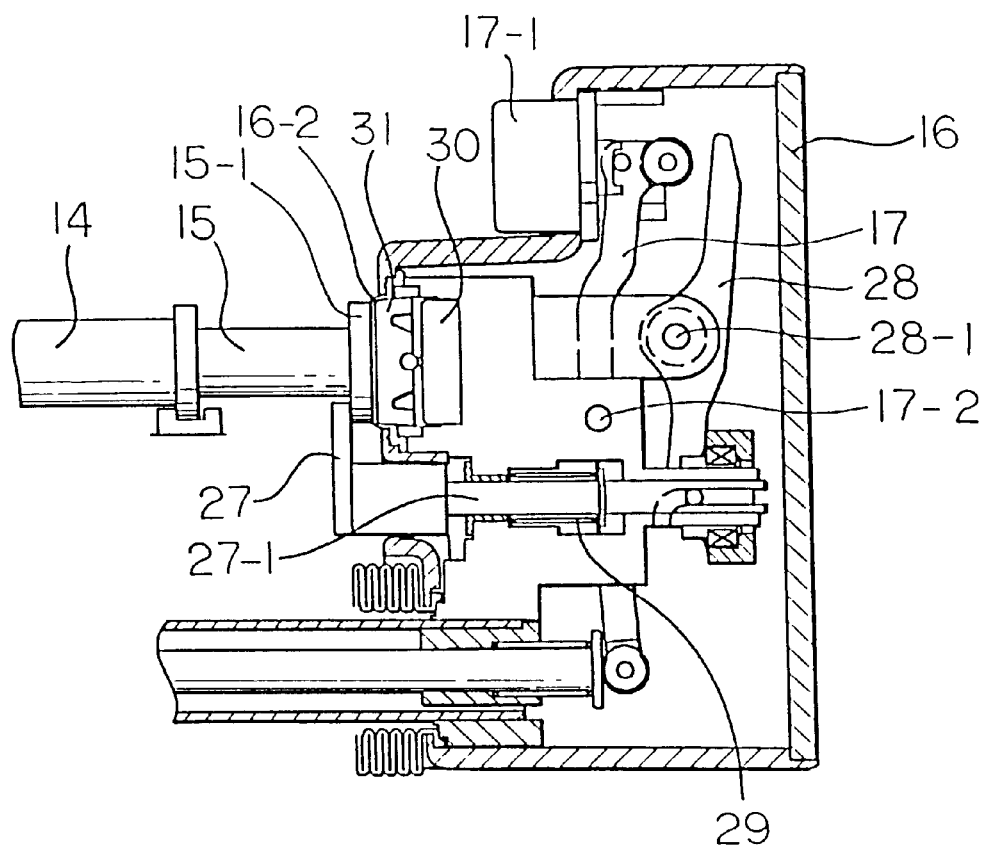
FIG. 12C illustrates a sectional view of an essential portion of the slider of a liquid infusion apparatus according to another embodiment of the present invention.

Another embodiment of the liquid infusion apparatus according to the present invention will be explained with reference to FIGS. 12A~12C. FIGS. 12A~12C each shows an enlarged cross section of essential portions of the slider 16. FIG. 12A shows a state that the holding arms 27 are opened and the flange of the plunger 15 is not mounted on the slider 16. FIG. 12B shows a state that the holding arms 27 are closed. FIG. 12C shows a state that the flange 15-1 of the plunger 15 is held by the holding arms 27. In order to avoid the complexity, the explanation of the driving means for the holding arms 27 is omitted.

In FIGS. 12A~12C, a reference numeral 30 denotes a pressure sensor and 31 denotes a pressure transmitting portion.

As shown in FIGS. 12A and 12B, the pressure sensor 30 is fixed to the slider 16, and a pressure receiving portion thereof is connected to the contact portion 16-2 through the pressure transmitting portion 31. In FIGS. 12A and 12B, the holding arms 27 are not contacted with the contact portion 16-2 of the slider, so that no pressure is applied to the pressure sensor 30.

In FIG. 12C, the flange 15-1 of the plunger is contacted with the contact portion 16-2 of the slider, the holding arms 27 are closed, and the holding arms 27 urge the flange 15-1 of the plunger to the contact portion 16-2 of the slider with the force of return springs 29. In this state, an output corresponding to the force of the return spring 29 is generated from the pressure sensor 30, because the flange 15-1 of the plunger is pressed to the contact portion 16-2 by the return springs 29.

Figure 13:
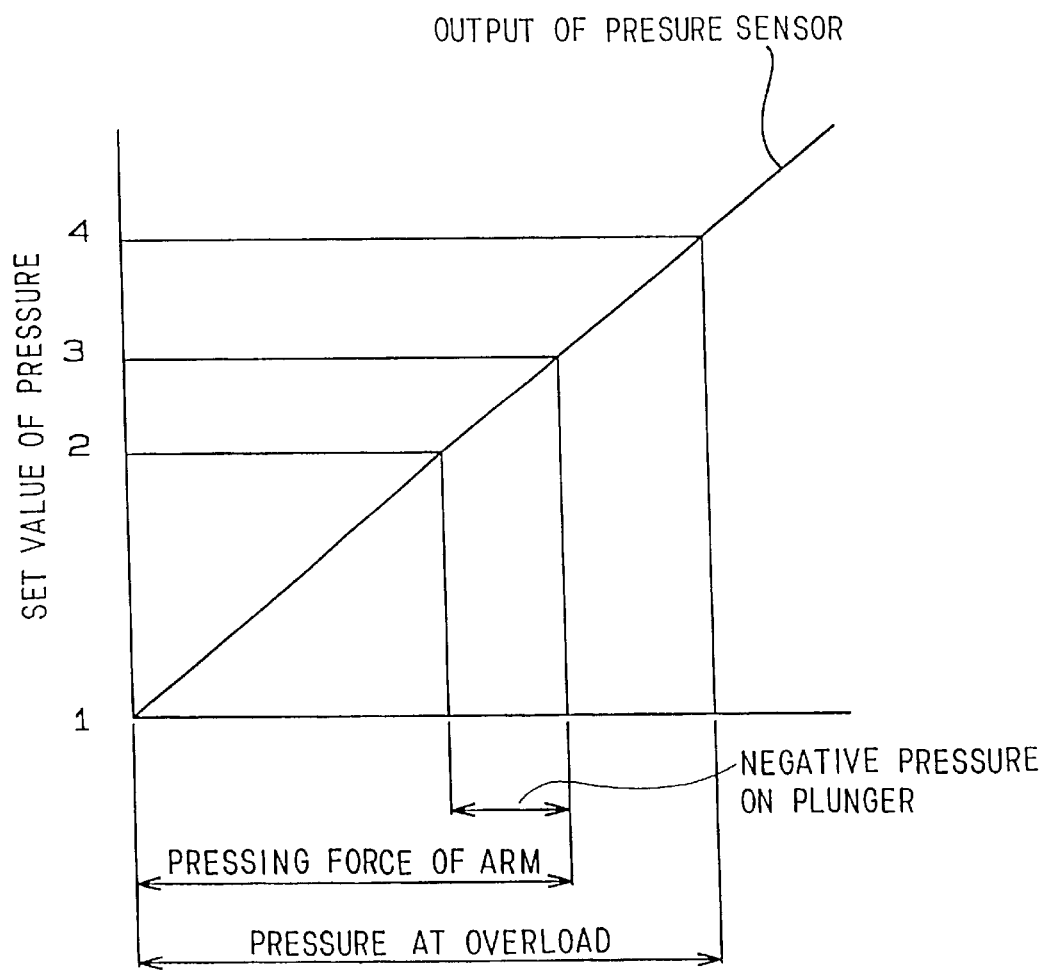
FIG. 13 illustrates a diagram showing a property of a pressure sensor of the liquid infusion apparatus according to another embodiment of the present invention.

FIG. 13 is a diagram showing the relation between the pressure applied to the pressure sensor 30 and the output thereof, and a point 1 of the ordinate corresponds to zero pressure and points 2, 3, 4 each corresponds to each pressure of the operation states. In FIG. 13, the point 1 of the ordinate shows a state that the syringe is not mounted on the slider as shown in FIGS. 12A and 12B, so that no pressure is applied to the pressure sensor 30 and the output is zero. The point 3 of the ordinate shows a state that the flange 15-1 of the plunger is contacted with the contact portion 16-2 of the slider and pressed by the holding arms 27 for holding as shown in FIG. 12C, so that the output of the pressure sensor corresponds to the force of the return spring 29. In this state, the motor 5 is inoperative and the slider 16 does not urge the plunger 15.

When the motor 5 is rotated in a predetermined direction at a predetermined speed in the state shown in FIG. 12C, the slider 16 engaged with the feed screw 7 urges the plunger 15 in the predetermined direction at a predetermined speed to exhaust the liquid. The output of the pressure sensor 30 is increased to a value more than the point 3 corresponding to the value of pressure required normally to exhaust liquid, so that the maximum pressure is determined as a point 4. The point 2, for example, is determined between the points 3 and 1 in order to detect the negative pressure applied to the plunger. The points 1, 2, 3 and 4 shown in FIG. 13 are set in a comparison circuit (not shown) and compared with the output of the pressure sensor 30 to generate processing signals corresponding to each state.

When the output of the pressure sensor 30 reaches to the point 1, a signal indicating that no syringe is set is generated. When the output of the pressure sensor 30 reaches to a value more than the point 3, but less than the point 4, a signal indicating that the operation is normal is generated. When the output of the pressure sensor 30 reaches to a value more than the point 4, a signal indicating the overload state is generated. When the output of the pressure sensor 30 reaches to a value less than the point 2, a signal indicating that the negative pressure is applied to the plunger is generated.

According to the liquid infusion apparatus of the present invention having the above construction, by comparing the output of the pressure sensor with the values set in the comparison circuit, signals indicating the overload state, out of syringe state, and negative pressure generating state, respectively, can be generated, so that the liquid infusion operation can be carried out safely.

Figure 14A:
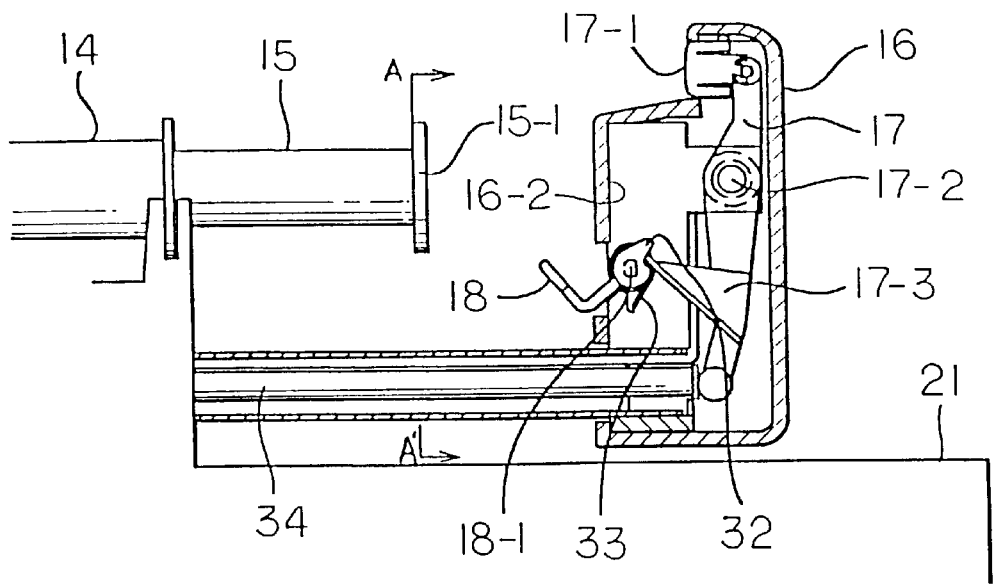
FIG. 14A illustrates a view of an essential portion in a state that the end of the plunger is not yet held by the slider of a liquid infusion apparatus according to another embodiment of the present invention.
Figure 14B:
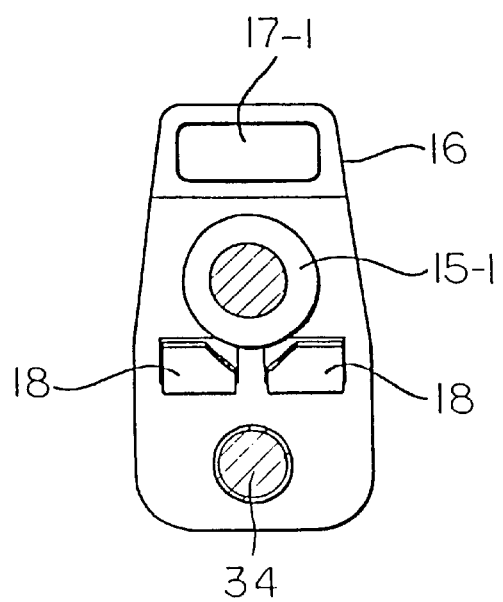
FIG. 14B illustrates a view, taken along lines A–A' of FIG. 14A.
Figure 15A:
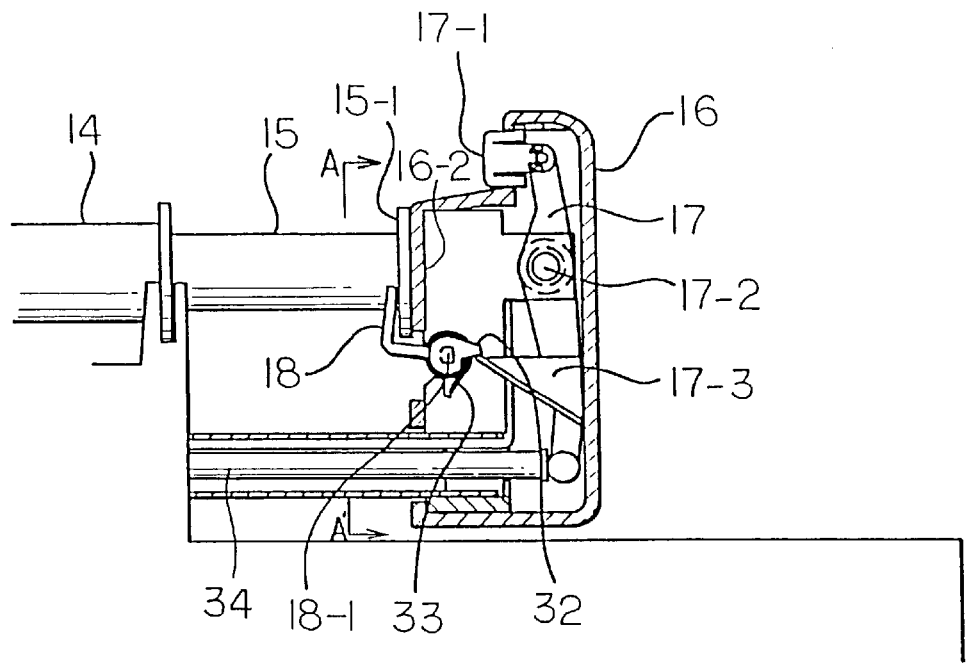
FIG. 15A illustrates a view of an essential portion in a state that the end of the plunger is held by the slider of a liquid infusion apparatus according to another embodiment of the present invention.
Figure 15B:
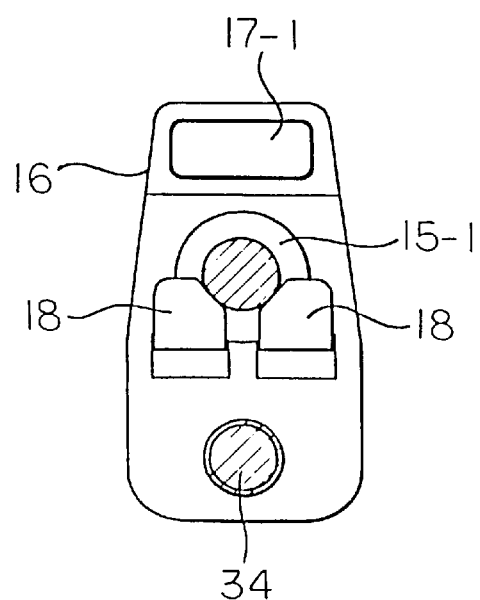
FIG. 15B illustrates a view, taken along lines A–A' of FIG. 15A.

Another embodiment of the liquid infusion apparatus according to the present invention will be explained with reference to FIGS. 14A, 14B, 15A and 15B. FIG. 14A shows a side view of essential portions of a state that the flange 15-1 of the plunger is not mounted on the slider 16. FIG. 14B shows a front view, taken along the lines A–A' of FIG. 14A and viewed in the direction of arrow. FIG. 15A shows a side view of essential portions of a state that the flange 15-1 of the plunger is held by the slider. FIG. 15B is a front view, taken along the lines A–A' of FIG. 15A and viewed in the direction of arrow.

In FIGS. 14A, 14B, 15A, and 15B, two holding arms 18 of the slider 16 for holding the flange of the plunger are supported by the shafts 18-1 rotatably freely and urged to rotate by springs 33 in the clockwise direction, each of said holding arms having a small projection 32 at the side face thereof. On the other hand, the lever 17 for operating an interlocking rod 34 interlocking with the releasing device (not shown) of the slider is supported by a shaft 17-2 rotatably freely, and a projection 17-3 is provided so as to project in the leftward direction from a position lower than said shaft 17-2 of the lever 17, so that when said push button 17-1 of the lever 18 is pushed, said arm 18 is rotated in the counter-clockwise direction against the force of the spring 33 by the tip end of the projection 17-3 through the small projection 32 provided at the side face of the arm 27. Accordingly, the holding arms 18 are opened to receive therein the flange 15-1 of the plunger easily.

As shown in FIGS. 15A and 15B, the projection 17-3 of the lever 17 is retracted, the holding arms 18 is rotated in the clockwise direction by the force of the spring 33, and the flange 15-1 of the plunger is brought into contact with the contact portion 16-2 of the slider 16 for holding, when the slider 16 is moved to a direction directing to the end portion of the plunger 15 of the syringe so that the contact portion 16-2 of the slider 16 is brought into contact with the end of the plunger, and the push button 17-1 of the lever 17 is returned.

Specifically, the flange 15-1 of the plunger can be held positively even if the size of the flange is varied according to the mechanical precision, because the flange 15-1 of the plunger is pressed to the contact portion 16-2 of the slider 16 by the holding arms 18 with the force of the springs 33 for holding.

In case that the syringe 14 is to be released from the main body 21 of the liquid infusion apparatus, the syringe 14 can be released easily, because the holding arms 18 are opened to release the flange of the plunger when the push button 17-1 of the lever 17 is pushed.

According to the above liquid infusion apparatus, the press holding and release of the flange can be carried out by the operation to push the slider release button when the syringe is mounted on or released from the main body of the liquid infusion apparatus, so that the handling is very easy and the load of the operator becomes small.

Figure 16A:
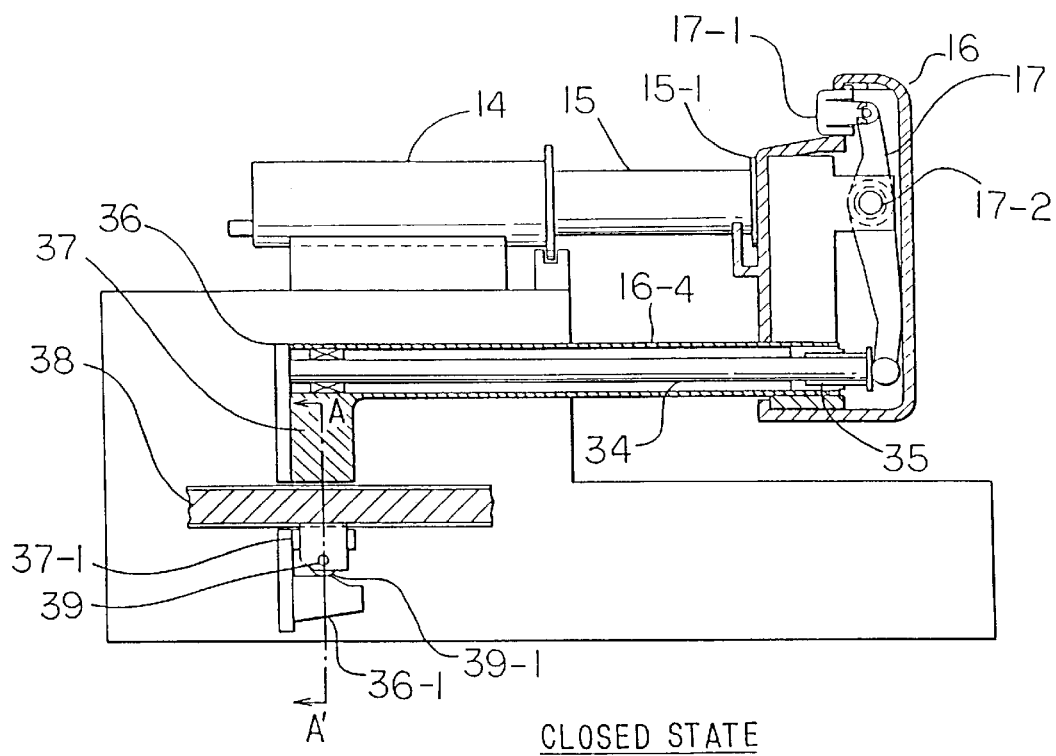
FIG. 16A illustrates a sectional view of an essential portion in a state that the end of the plunger is held by the slider of a liquid infusion apparatus according to another embodiment of the present invention.
Figure 16B:
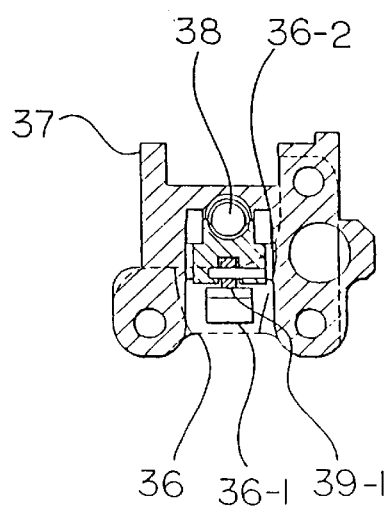
FIG. 16B illustrates a view, taken along lines A–A' of FIG. 16A.
Figure 17A:
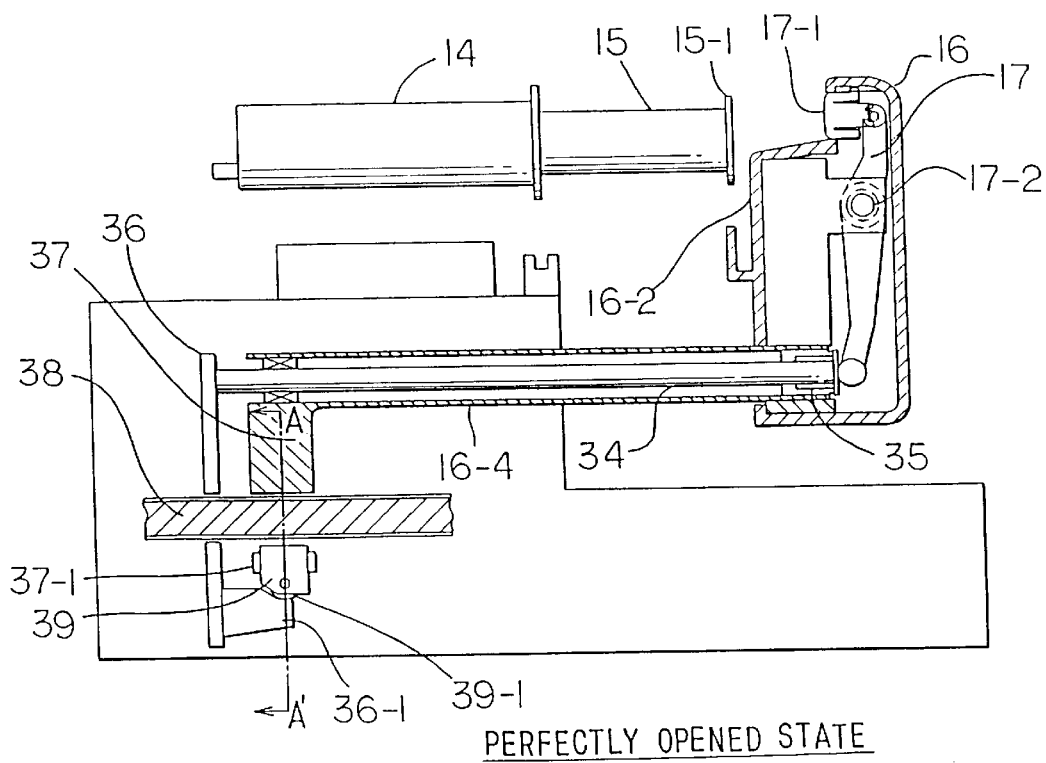
FIG. 17A illustrates a sectional view of an essential portion in a state that the end of the plunger is not yet held by the slider of the liquid infusion apparatus according to the embodiment shown in FIGS. 16A and 16B.
Figure 17B:
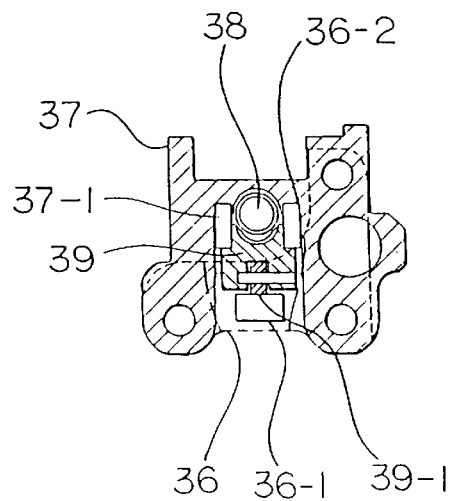
FIG. 17B illustrates a sectional view, taken along lines A–A' of FIG. 17A.

Another embodiment of the present invention will now be explained with reference to FIGS. 16A, 16B, 17A, 17B, 18A, 18B, 19A, 19B, 20A, 20B, 21A and 21B. FIGS. 16A and 16B show a state that a half-nut releasing device is engaged and a half-nut is engaged with the feed screw. FIG. 16A is a side view of essential portions of the apparatus according to the present invention. FIG. 16B is a cross section of the essential portion, taken along the lines A–A' of FIG. 16A. FIGS. 17A and 17B show a state that the half-nut is released. FIG. 17A is a side view of the essential portion of the apparatus. FIG. 17B is a cross section of the essential portion, taken along the lines A–A' of FIG. 17A.

In FIGS. 16A, 16B, 17A and 17B, reference numeral 16-4 denotes an extending portion of the slider 16, reference numeral 35 denotes a return spring for an interlocking rod 34, 36 denotes a half-nut releasing device, 36-1 denotes a releasing cam, 37 denotes a half-nut holding portion, 37-1 denotes a half-nut sliding groove, 37-2 denotes a release spring for the half-nut, 38 denotes a feed screw, 39 denotes a half-nut, and 39-1 denotes a bearing.

As shown in FIGS. 16A, 16B, 17A and 17B, the half-nut holding portion 37 is provided on the extending portion 16-4 of the slider 16 extending along the feed screw 38 movably freely with respect to the feed screw 38, and the half-nut sliding groove 37-1 extending normally to the feed direction of the feed screw 38 is provided at the half-nut holding portion 37. The half-nut 39 is inserted slidably into the sliding groove 37-1 to support the half-nut by the feed screw detachably, and the half-nut releasing device 36 is fixed on the tip end of the interlocking rod 34 having the return spring 35 arranged in parallel with the extending portion 16-4. The releasing cam 36-1 having a step extending to the forward direction of the interlocking rod 34 is formed on the half-nut releasing device 36 at a position facing the end portion of the half-nut 39, the bearing 39-1 provided at the end of the half-nut 39 is brought into contact with the releasing cam 36-1, and the half-nut 39 is urged to a releasing direction by a spring 36-2 for releasing.

As shown in FIGS. 17A and 17B, the releasing can of the half-nut releasing device 36 fixed to the interlocking rod 34 is moved leftwards, and the bearing 39-1 of the half-nut 39 is brought into contact with the lower step of the releasing cam 36-1, so that the half-nut 39 is separated from the feed screw 38 by the force of the spring 36-2, when the push button 17-1 of the releasing lever 17 is pushed, and the interlocking rod 34 is moved leftwards against the force of the return spring 35.

As shown in FIGS. 16A and 16B, the interlocking rod 34 is moved rightwards, and the bearing 39-1 of the half-nut 39 is brought into contact with the upper step of the releasing cam 36-1, so that the half-nut 39 is brought into engagement with the feed screw 38 against the force of the spring 36-2, when the push button 17-1 of the releasing lever 17 is retracted, and the interlocking rod 34 is moved rightwards by the force of the return spring 35.

As a result, the half-nut 39 is prevented from floating from the feed screw, because the half-nut 39 is urged in the direction normal to the feeding direction of the feed screw by the upper step of the releasing cam.

Figure 18A:
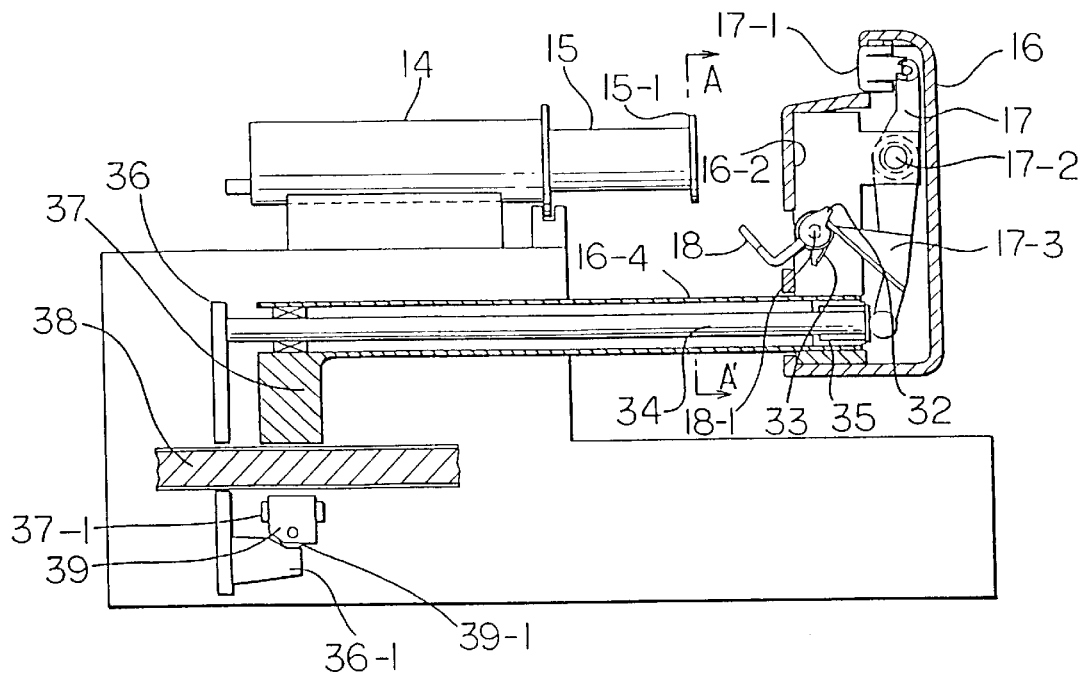
FIG. 18A illustrates a sectional view of an essential portion in a state that the end of the plunger is not yet held by the slider of a liquid infusion apparatus according to another embodiment of the present invention.
Figure 18B:
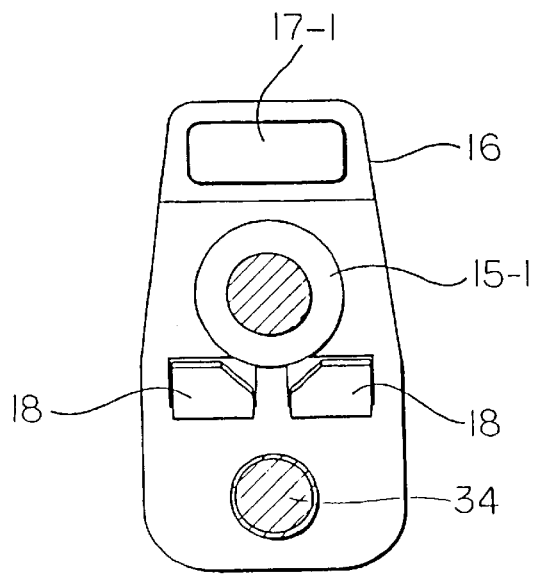
FIG. 18B illustrates a view, taken along lines A–A' of FIG. 18A.
Figure 19A:
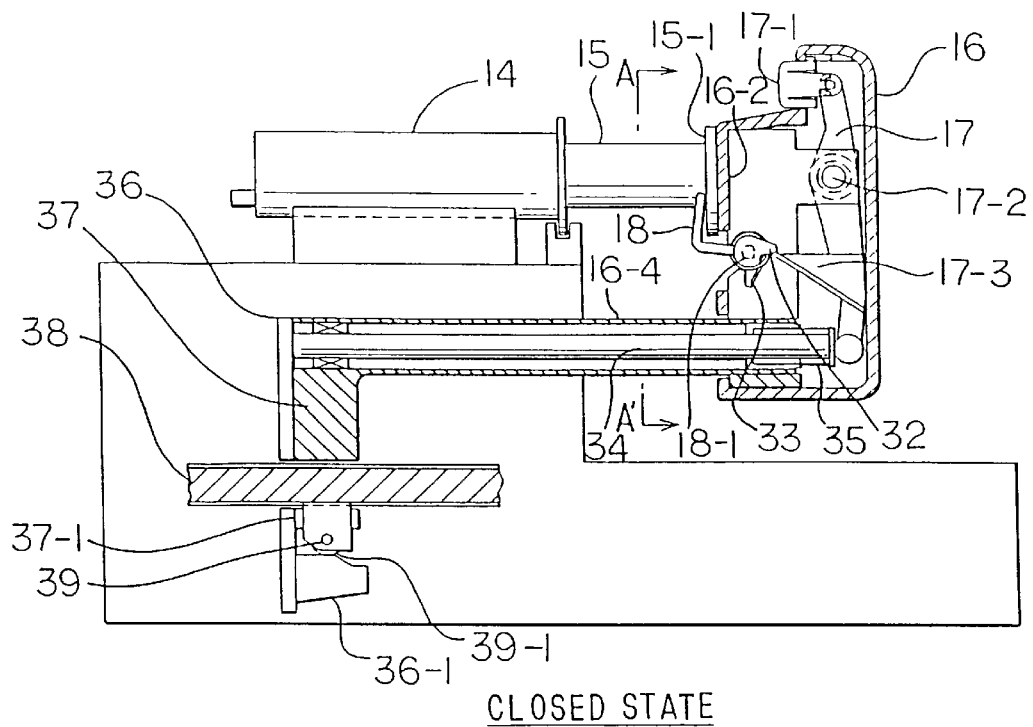
FIG. 19A illustrates a sectional view of an essential portion in a state that the end of the plunger is held by the slider of the liquid infusion apparatus according to the embodiment shown in FIGS. 18A and 18B.
Figure 19B:
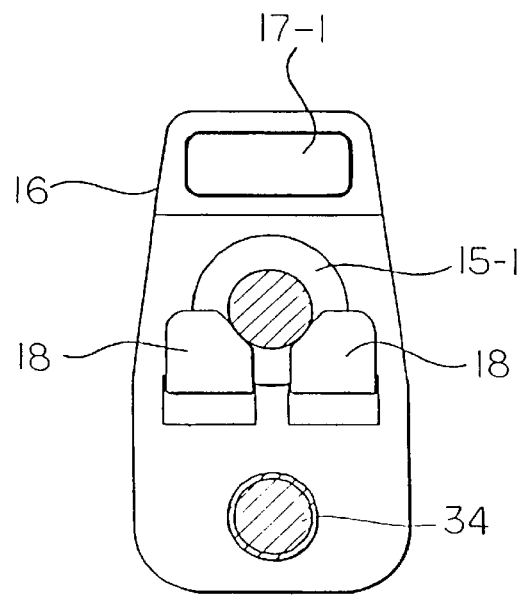
FIG. 19B illustrates a view, taken along lines A–A' of FIG. 19A.

Another embodiment of the present invention wherein both of the half-nut releasing device 36 and the holding arm for press holding the flange of the plunger by the slider 16 are provided will now be explained. FIGS. 18A and 18B show a state that the flange of the plunger is not yet held by the slider 16. FIG. 18A is a sectional side view of the essential portion. FIG. 18B is a view, taken along the lines A–A' of FIG. 18A. FIGS. 19A and 19B show a state that the flange of the plunger is held by the slider 16. FIG. 19A is a sectional side view of the essential portion. FIG. 19B is a view, taken along the lines A–A' of FIG. 19A.

In FIG. 18, the slider 16 is arranged at a position remote from the plunger 16, and when the push button 17-1 is pushed the slider releasing lever 17 is rotated around the shaft 17-2 and the projection 32 of the arm 18 is pushed by the tip end of the projection 17-3 at the left side of the slider releasing lever 17, so that the arm 18 is rotated in the counter-clockwise direction against the force of the return spring 33. As a result, the tip end of the arm 18 is lowered from the position of the flange 15-1 of the plunger so that the flange 15-1 of the plunger can be passed easily through the arms. As shown in FIG. 18B, the holding arms 18 are positioned at the outside of the flange 15-1 of the plunger. On the other hand, the bearing 39-1 is brought into contact with the lower step of the releasing cam 36-1, and the half-nut 39 is lowered by the force of the spring 36-2 and separated from the feed screw 38, so that the slider can be moved freely in the moving direction of the plunger, when the interlocking rod 34 is moved in the leftward direction against the force of the return spring 35 by the other end of the slider releasing lever 17 to move the half-nut releasing device 36 connected to the interlocking rod 34 in the leftward direction.

As shown in FIG. 19A, the projection 17-3 of the releasing lever 17 is retracted, and the holding arm 18 is rotated in the clockwise direction, so that the flange 15-1 of the plunger is pressed to the contact portion 16-2 of the slider 16 and held by the tip end of the holding arm 18, when the slider 16 is moved toward the end portion of the plunger to bring the contact portion 16-2 of the slider 16 into contact with the end portion of the flange 15-1 of the plunger 15, and the push button 17-1 of the releasing device of the slider is released.

On the other hand, when the interlocking rod 34 to which the other end of the slider releasing lever 17 is contacted is moved in the rightward direction by the force of the return spring 35, the half-nut releasing device 36 connected to the interlocking rod 34 Is also moved in the rightward direction, so that the bearing 39-1 of the half-nut is brought into contact with the upper step of the releasing cam 36-1, and the half-nut 39 is moved upwardly against the spring 36-2 and brought into engagement with the feed screw 38. As the upper step of the releasing cam 36-1 is formed in parallel with the feed screw, the precise feeding can be attained, because the floating movement in the radial direction of the half-nut is prevented even if a load is applied to the feed screw 38.

Another embodiment of the present invention wherein both of the half-nut releasing device 36 and the holding arm for press holding the flange of the plunger are provided on the slider will be explained.

Figure 20A:
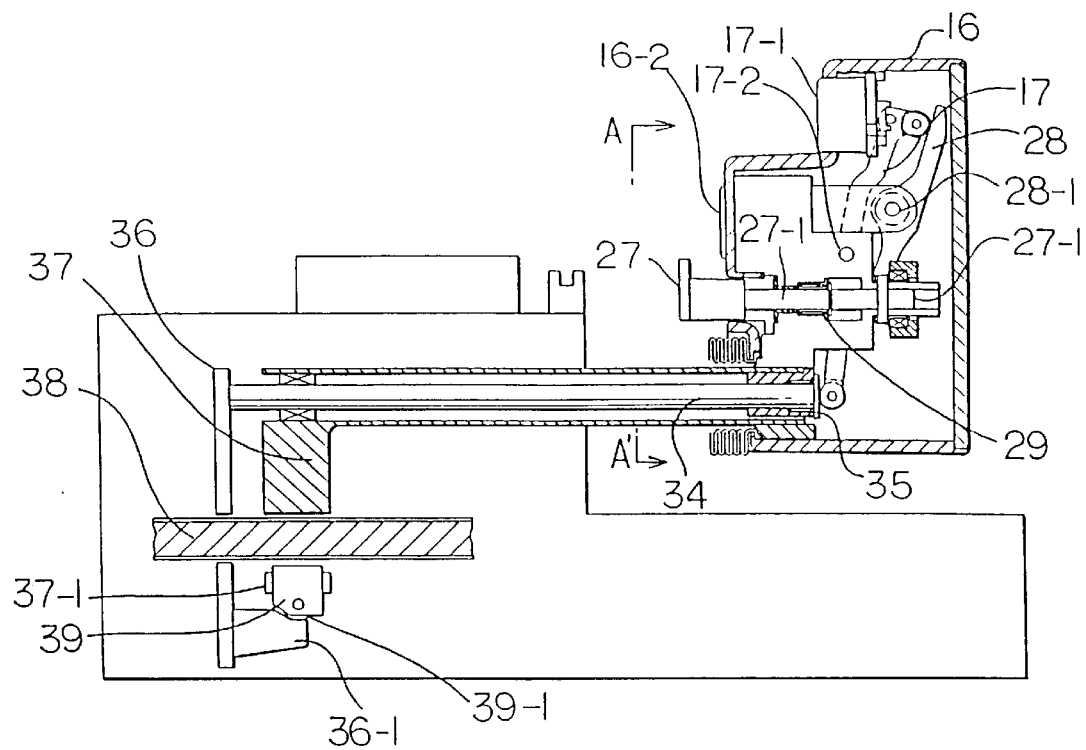
FIG. 20A illustrates a sectional view of an essential portion in a state that the end of the plunger is not yet held by the slider of a liquid infusion apparatus according to another embodiment of the present invention.
Figure 20B:
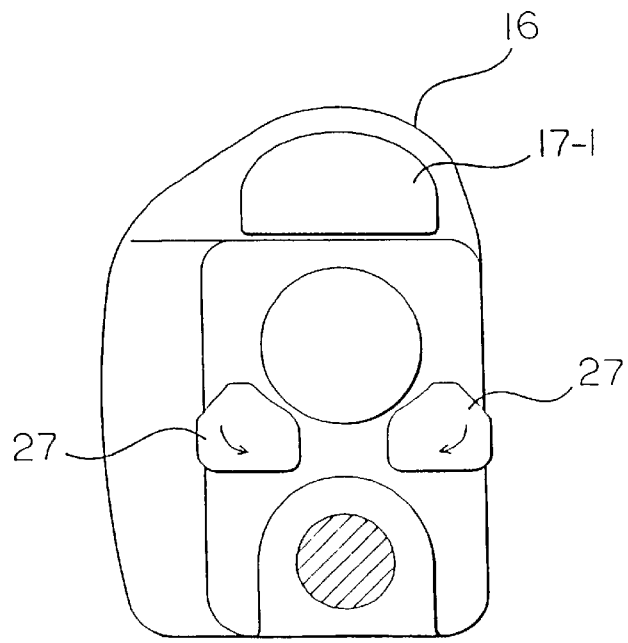
FIG. 20B illustrates a view, taken along lines A–A' of FIG. 20A.

FIGS. 20A and 20B show a state that the flange of the plunger of the syringe is not yet held by the slider 16. FIG. 20A is a side view of essential portions. FIG. 21B is a view, taken along the lines A–A' of FIG. 21A.

As shown in FIGS. 20A and 20B, the slider is 16 is positioned remote from the flange 15-1 of the plunger of the syringe 14, and two holding arms 27 supported by the shafts 27-1 are separated from the slider 16 by the internal mechanism of the slider 16, rotated in the directions of arrows and opened so that the flange 15-1 of the plunger can be brought into contact with the contact portion 16-2.

Figure 21A:
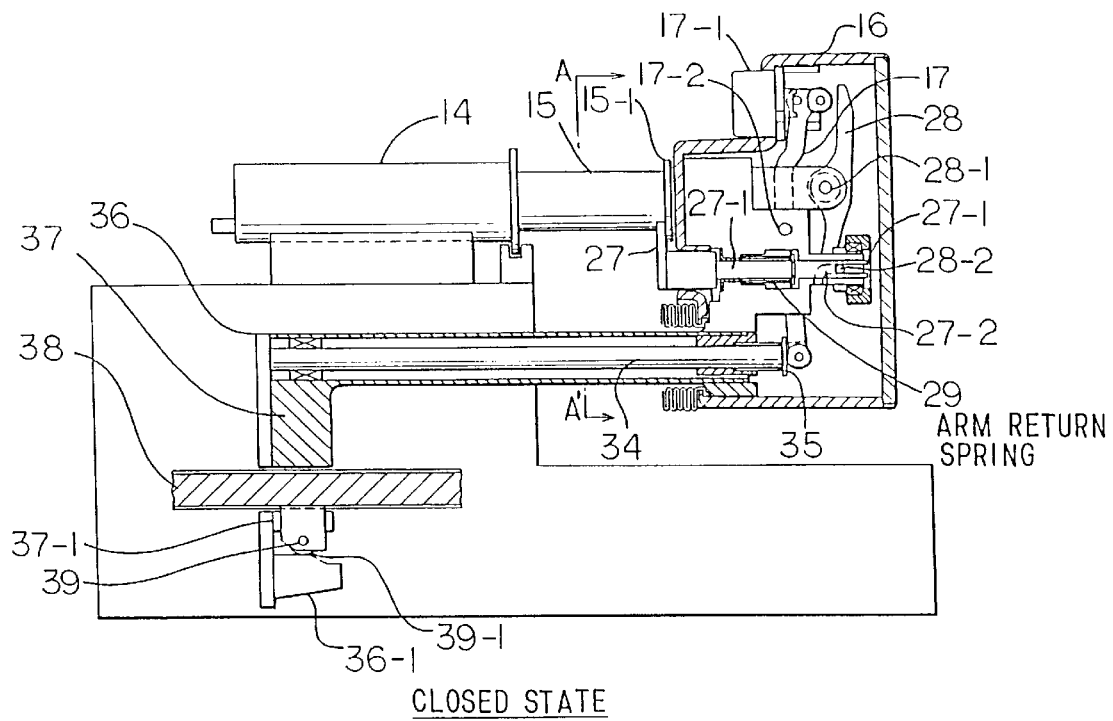
FIG. 21A illustrates a sectional view of an essential portion in a state that the end of the plunger is held by the slider of the liquid infusion apparatus according to the embodiment shown in FIGS. 20A and 20B.
Figure 21B:
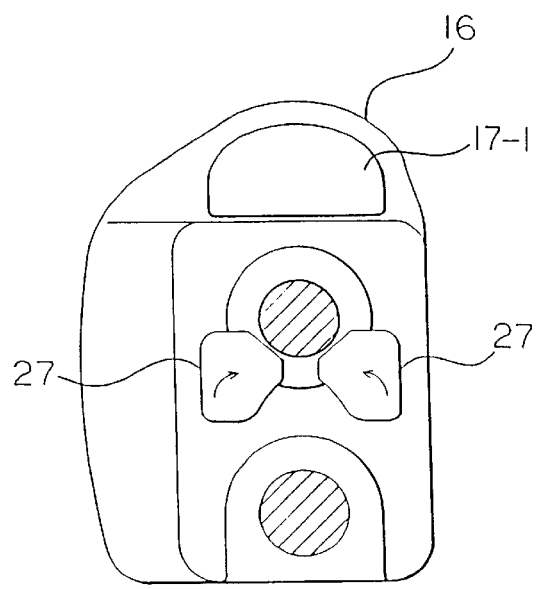
FIG. 21B illustrates a view, taken along lines A–A' of FIG. 21A.

As shown in FIGS. 21A and 21B, two holding arms 27 supported by the shafts 27-1 approach the slider 16 and are rotated in the directions of arrows and closed, so that the flange 15-1 of the plunger is pressed to and held by the contact portion 16-2 of the slider 16, when the slider 16 is moved toward the plunger to bring the contact portion 16-2 into contact with the flange 15-1 of the plunger, and the release button 17-1 is retracted.

This mechanism is shown detailedly in FIGS. 20A, 20B, 21A and 21B. FIG. 20A is a cross section of the essential portion in a state that the plunger is not yet contacted with the slider 16. FIG. 20B is a side view, taken along the lines A–A' of FIG. 20A. FIG. 20B shows a state that the release button 17-1 is pushed, and the interlocking rod 34 is moved in the leftward direction, so that the bearing 39-1 of the half-nut is brought into contact with the lower step of the releasing cam 36, and the half-nut 39 is lowered by the force of the spring 36-2 to release the engagement of the feed screw 38. Two holding arms 27 are supported rotatably freely by the shafts 27-1 and movably in the forward direction of the slider 16. A guide groove for rotation is formed at one side of the shaft 27-1 opposite to the other side of the shaft 27-1 on which the holding arm 27 is mounted. The holding arm 27 is urged to the plunger contact surface of the slider by the return spring 29.

The driving lever 28 for driving the holding arm 27 supported by the shaft 17-2 is rotated in the clockwise direction when the releasing button 17-1 is pushed. The shaft 27-1 is moved in the leftward direction against the return spring 29 and rotated by the action of the guide groove 27-2 because the engaging pin 28-2 provided at one end of the lever 28 is engaged with the guide groove 27-2 provided on the shaft 27-1 of the holding arm 27, so that as shown in FIG. 20B the holding arms 27 are opened and the flange of the plunger can be brought into contact with the contact surface of the slider 16.

In FIGS. 20A and 20B, the releasing lever 17 is restored, and the interlocking rod 34 is moved in the rightward direction by the force of the return spring 35, so that the bearing 39-1 is brought into contact with the upper step of the releasing cam 36-1 of the half-nut releasing device 36, and the half-nut 39 is brought into engagement with the feed screw 38, when the slider 16 is moved and contacted with the flange of the plunger, and the released button 17-1 is restored, as shown in FIGS. 21A and 21B. On the other hand, when the release button 17-1 is restored, the driving lever 28 for the holding arm 27 is rotated in the counter-clockwise direction, the engaging pin 28-2 engaged with the guide groove 27-2 of the shaft 27-1 is moved in the rightward direction, and the holding arm 27 is rotated by the force of the spring 29, so that the flange is pressed to and held by the contact portion 16-2 of the slider 16. The flange of the plunger can be held positively by the slider, because the holding arm 27 is attracted toward the plunger contact surface of the slider by the force of the return spring 29 while the shaft 27-1 is rotated.

Further, the cross section of the tooth of the feed screw 34 is inclined to a plane normal to the feeding direction of the screw, so that the feed screw can be manufactured by the form rolling process etc. economically with high precision. On the contrary, the half-nut 39 may be floated in the radial direction thereof on loading. However, the upper step of the release cam 36-1 is formed in parallel with the screw 38 and urges the half-nut 39 toward the screw 38, so that the half-nut 39 is prevented from floating to ensure the precise feeding. Further, if the cross section of the tooth of the feed screw 38 is saw tooth shape and the vertical surface thereof is determined as the forward side, the floating of the half-nut 39 on loading can be prevented, and the screw can be manufactured economically and easily.

In the liquid infusion apparatus having the above construction, the engagement and disengagement of the slider with the feed screw can easily be carried out by the operation of the slider release button, and the flange of the plunger can be pressed to and held by the rotatable slider.

Figure 22:
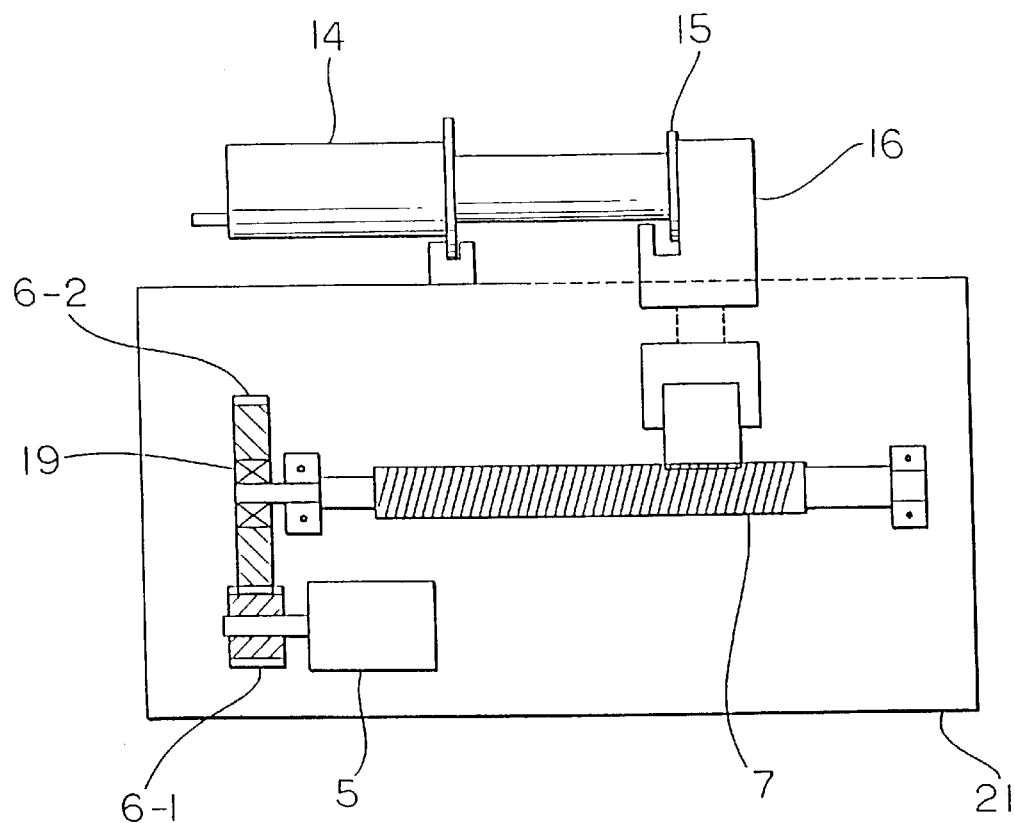
FIG. 22 illustrates a side view showing a liquid infusion apparatus according to the other embodiment of the present invention.
Figure 23:
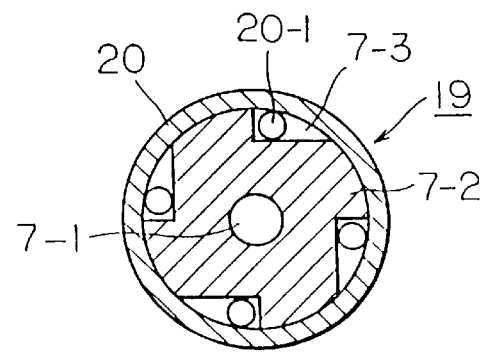
FIG. 23 illustrates a section view of a one-way clutch for use in the liquid infusion apparatus according to the present invention.

In the other embodiment of a liquid infusion apparatus shown in FIG. 22, the feed screw 7 is connected to the rotary shaft of the electric motor 5 through a pinion 6-1, a one-way clutch 19 and a large gear 6-2. As said one-way clutch, a conventional clutch as shown in FIG. 23 can be used. The clutch comprises a cylinder 7-2 fixed coaxially to an axis 7-1 of the feed screw 7, a plurality of triangular grooves 7-3 formed on the outer periphery of the cylinder 7-2, an outer cylinder 20 fixed to said large gear 6-2, the inner peripheral surface of said outer cylinder 20 facing the outer peripheral surface of said cylinder 7-2, and balls 20-1 each inserted into a space formed between the inner peripheral surface of said outer cylinder 20 and said triangular groove 7-3.

In the liquid infusion apparatus shown in FIG. 22, when the electric motor 5 is rotated in the predetermined direction (in the clockwise direction, for example), the feed screw 7 is rotated by the electric motor 5 through the one-way clutch 19, so that the slider 16 is urged to move the plunger 15 in the liquid exhausting direction and thus the liquid infusion apparatus is operated correctly. The one-way clutch 19 slips and the rotation of the electric motor 5 is not transmitted to the feed screw 7, if the electric motor 5 is rotated reversely (counter-clockwise direction) for some reason, and accordingly such a wrong operation that the plunger 15 is moved reversely (suction direction) by the slider can be prevented.

The above liquid infusion apparatus has such an excellent function that the wrong operation, such as the reverse moving of the plunger can be prevented even if the electric motor is rotated reversely due to the electric noises or the like.

INDUSTRIAL APPLICABILITY

As stated above, the liquid infusion apparatus of the present invention is useful for the oscillating device of the plunger of the syringe.

The scope of the present invention should not be limited to the above embodiments and should be defined by the terms of the claims appended hereto.

What is claimed is:

1. In a liquid infusion apparatus having a feed screw driven by a prime mover and a slider movable linearly and engaged with said feed screw so as to push a plunger of a syringe for exhausting liquid in the syringe, the improvement characterized by comprising a holding arm for pushing a flange of said plunger in a direction reverse to a pushing direction of the plunger toward a plunger holding portion of said slider for holding, a pressure sensor provided at said plunger holding portion of the slider, and a processing circuit for comparing an output of said pressure sensor with a plurality of reference values to generate a processing signal.

2. The liquid infusion apparatus of claim 1, wherein said plural reference values comprise:
   a first value corresponding to an output of said pressure sensor in a state that the flange of the plunger is held by the plunger holding portion of the slider; and
   a second value corresponding to an output of said pressure sensor at the maximum desired pressure within the syringe.

3. The liquid infusion apparatus of claim 1, wherein said plural reference values comprise:
   a first value corresponding to an output of said pressure sensor in a state that the flange of the plunger is held by the plunger holding portion of the slider; and
   a second value corresponding to an output of said pressure sensor at the maximum desired pressure within the syringe;
   wherein said reference values comprise means for generating:
      (1) a signal indicating a state that no syringe is set when the output of the pressure sensor is less than said first value;
      (2) a signal indicating a normal state when the output of the pressure sensor is between said first and second reference values; and
      (3) a signal indicating an overload state when the output of the pressure sensor is greater than said second reference value.

4. The liquid infusion apparatus of claim 1, wherein said plural reference values comprise:
   a first value corresponding to an output of said pressure sensor in a state that the flange of the plunger is not yet held by the plunger holding portion of the slider;
   a second value corresponding to an output of said pressure sensor in a state that the flange of the plunger is held by the plunger holding portion of the slider; and
   a third value corresponding to an output of said pressure sensor at the maximum desired pressure within the syringe.

5. The liquid infusion apparatus of claim 1, wherein said plural reference values comprise:
   a first value corresponding to an output of said pressure sensor in a state that the flange of the plunger is not yet held by the plunger holding portion of the slider;
   a second value corresponding to an output of said pressure sensor in a state that the flange of the plunger is held by the plunger holding portion of the slider; and
   a third value corresponding to the maximum desired pressure within the syringe;
   wherein said reference values comprise means for generating:
      (1) a signal indicating a state that no syringe is set when the output of the pressure sensor is less than said first value;
      (2) a signal indicating a vacuum state within the syringe when the output of the pressure sensor is between said first and second reference values
      (3) a signal indicating a normal state when the output of the pressure sensor is between said second and third reference values; and (4) a signal indicating an overload state when the output of the pressure sensor is greater than said third reference value.

6. In a liquid infusion apparatus having a feed screw driven by a prime mover and a slider movable linearly and engaged with said feed screw so as to push a plunger of a syringe for exhausting liquid in the syringe, the improvement characterized by comprising a holding arm for pushing a flange of said plunger in a direction reverse to a pushing direction of the plunger toward a plunger holding portion of said slider for holding, a pressure sensor provided at said plunger holding portion of the slider, and a processing circuit for comparing an output of said pressure sensor with a plurality of reference values to generate a processing signal;

wherein said plural reference values are 1, 2, 3 and 4, and set in a processing circuit for comparing, the value 1 corresponding to an output of said pressure sensor in a state that the flange of the plunger is not yet held by the plunger holding portion of the slider, the value 3 corresponding to an output of said pressure sensor in a state that the flange of the plunger is held by the plunger holding portion of the slider, which is more than the output of the value 1, the value 4 corresponding to the maximum output of said pressure sensor, which is more than the output of the value 3, and the value 2 corresponding to an output of said pressure sensor which is more than the output of the value 1, but less than the output of the value 3, respectively, and further comprising means for generating (1) a signal indicating a state that no syringe is set when the output of the pressure sensor becomes to the value 1, (2) a signal indicating a normal state when the output of the pressure sensor becomes to a value more than the value 3, but less than the value 4, (3) a signal indicating an overload state when the output of the pressure sensor becomes to a value more than the value 4, and (4) a signal indicating a case that a negative pressure is applied on the plunger when the output of the pressure sensor becomes to the value 2, respectively.

7. In a liquid infusion apparatus having a feed screw driven by a prime mover and a slider movable linearly, which is engaged with said feed screw so as to push a plunger of a syringe for exhausting liquid in the syringe, the improvement characterized by comprising a holding means for holding a flange of said plunger by the slider, which is fixed to a supporting shaft movable in a moving direction of the slider and supported rotatably freely, wherein said supporting shaft is rotated so as to separate said holding means from said flange when said holding means is moved so as to go away from the slider, and said supporting shaft is rotated so as to bring the holding means into engagement with said flange when said holding means is approached to the slider.

8. The liquid infusion apparatus according to claim 7, wherein said holding means is capable of positive engagement with flanges of varied thickness.

9. In a liquid infusion apparatus having a feed screw driven by a prime mover and a slider movable linearly, which is engaged with said feed screw so as to push a plunger of a syringe for exhausting liquid in the syringe, the improvement characterized by comprising a lever supported rotatably freely by a first shaft arranged horizontally and normally to a moving direction of said slider, a push button provided at one end of said lever so as to project from said slider, a slider releasing device, an interlocking rod interlocking with said slider releasing device, the other end of said lever being contacted with said interlocking rod, holding means supported by said slider rotatably by a second shaft for press holding the flange of the plunger by the slider, a spring for urging the holding means to rotate in the clockwise direction, and interlocking means for interlocking said holding means with said lever.

10. The liquid infusion apparatus as claimed in claim 9, wherein said interlocking means has a spring for urging said holding means to rotate in the clockwise direction.

11. The liquid infusion apparatus according to claim 9, wherein said holding means releases said flange upon operation of said push button.

12. In a liquid infusion apparatus having a feed screw driven by a prime mover and a slider movable linearly, which is engaged with said feed screw so as to push a plunger of a syringe for exhausting liquid in the syringe, the improvement characterized by comprising a lever supported rotatably freely by a first shaft arranged horizontally and normally to a moving direction of said slider, a push button provided at one end of said lever so as to project from said slider, a slider releasing device, an interlocking rod interlocking with said slider releasing device, the other end of said lever being contacted with said interlocking rod, holding means supported by said slider rotatably by a second shaft, which is in parallel to said first shaft for press holding the flange of the plunger by the slider, a spring for urging the holding means to rotate in the clockwise direction, and interlocking means for interlocking said holding means with said lever;

wherein said interlocking means has a projection provided on the other side of said lever which is brought into engagement with a small projection provided on an end of said holding arm, so that said holding arm is rotated in the counter-clockwise direction by said projection.

13. In a liquid infusion apparatus having a feed screw driven by a prime mover and a slider movable linearly, which is engaged with said feed screw so as to push a plunger of a syringe for exhausting liquid in the syringe, the improvement characterized by comprising first means consisting of a releasing lever supported rotatably freely by a first shaft of the slider, a push button provided at one end of said releasing lever so as to project from said slider, a half-nut releasing device engaging with the feed screw, a pressing portion provided at the other end of the releasing lever for pressing an end of an interlocking rod extending in parallel with the feed screw, and a first spring for restoring said interlocking rod; and second means consisting of a half-nut holding portion movable freely with respect to the feed screw, which is provided an extending portion extending in parallel with the interlocking rod and connected as a unit to said slider, a half-nut sliding groove extending normal to the forward direction of the feed screw, formed on the half-nut holding portion, a half-nut inserted slidably into said sliding grove and supported detachably from the feed screw, and a half-nut releasing device fixed to the other end of said interlocking rod;

wherein said half-nut releasing device has a releasing cam having at a position facing a surface opposite to a screw surface of the half-nut a step portion in the forward direction of the interlocking rod, and a second spring provided on the half-nut holding portion for urging in the releasing direction the half-nut.

14. The liquid infusion apparatus as claimed in claim 13, further comprising a holding arm supported rotatably freely by a second shaft, which is in parallel with said first shaft for press holding a flange of the plunger by the slider, a third spring for urging the holding arm to rotate in the clockwise direction, and a projection on said releasing lever, which is brought into engagement with a small projection provided on an end of said holding arm.

15. The liquid infusion apparatus as claimed in claim 13, further comprising a holding arm supported rotatably freely and movably in the slider moving direction by a supporting shaft for holding a flange of a plunger by the slider, wherein said supporting shaft is rotated so as to separate said holding arm from said flange when said holding arm is moved so as to go away from the slider interlocking with said releasing lever, and said supporting shaft is rotated so as to bring the holding arm into engagement with said flange when said holding arm is approached to the slider.

16. The liquid infusion apparatus as claimed in claim 13, wherein the cross section of the tooth of the feed screw is inclined to a plane normal to the feeding direction of the feed screw.

17. The liquid infusion apparatus as claimed in claim 13, wherein the cross section of the tooth of the feed screw is saw tooth shape.

18. In a liquid infusion apparatus having a feed screw driven by a prime mover and a slider movable linearly, which is engaged with said feed screw so as to push a plunger of a syringe for exhausting liquid in the syringe, the improvement characterized by comprising means for transmitting a driving force from the prime mover only in a syringe pushing direction inserted between the feed screw and the prime mover.

19. The liquid infusion apparatus as claimed in claim 18, wherein said means for transmitting the driving force is a one-way clutch.

* * * * *